(12) United States Patent
Gerber et al.

(10) Patent No.: US 10,272,363 B2
(45) Date of Patent: Apr. 30, 2019

(54) UREASE INTRODUCTION SYSTEM FOR REPLENISHING UREASE IN A SORBENT CARTRIDGE

(71) Applicant: Medtronic, Inc., Minneapolis, MN (US)

(72) Inventors: Martin T. Gerber, Maple Grove, MN (US); Christopher M. Hobot, Tonka Bay, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 589 days.

(21) Appl. No.: 14/641,673

(22) Filed: Mar. 9, 2015

(65) Prior Publication Data

US 2015/0367059 A1 Dec. 24, 2015

Related U.S. Application Data

(60) Provisional application No. 62/016,613, filed on Jun. 24, 2014, provisional application No. 62/077,171, filed on Nov. 7, 2014.

(51) Int. Cl.
*B01D 15/08* (2006.01)
*A61M 1/16* (2006.01)
*B01D 61/24* (2006.01)

(52) U.S. Cl.
CPC ........... *B01D 15/08* (2013.01); *A61M 1/1696* (2013.01); *A61M 2202/0057* (2013.01);
(Continued)

(58) Field of Classification Search
CPC ........ A61M 1/1696; A61M 2202/0057; A61M 2202/0498; A61M 2205/12; A61M 2205/3337; B01D 15/08; B01D 61/243
See application file for complete search history.

(56) References Cited

U.S. PATENT DOCUMENTS 2,703,313 A 1/1950 Gill
3,608,729 A 9/1971 Haselden
(Continued)

FOREIGN PATENT DOCUMENTS

CN 104936633 9/2015
EP 711182 B1 6/2003
(Continued)

OTHER PUBLICATIONS

PCT/US2014/065950 International Search Report and Written Opinion dated Feb. 24, 2015.
(Continued)

*Primary Examiner* — John Kim
(74) *Attorney, Agent, or Firm* — Kenneth Collier; Roger Hahn

(57) ABSTRACT

An apparatus and method for replenishing urease in a sorbent cartridge for use in sorbent dialysis. The system is configured to allow insertion of a urease pouch, injection of a urease solution, or addition of a urease cartridge, into a dialysis cabinet containing a dialysis flow loop. The urease can be dissolved and the resulting urease solution added to the sorbent cartridge in the flow loop to replenish the urease within the sorbent cartridge. The sorbent cartridge can also comprise other, rechargeable, sorbent materials for removing toxins other than urea from spent dialysate.

12 Claims, 12 Drawing Sheets

(52) U.S. Cl.
CPC . *A61M 2202/0498* (2013.01); *A61M 2205/12* (2013.01); *A61M 2205/3337* (2013.01); *B01D 61/243* (2013.01)

(56) References Cited

U.S. PATENT DOCUMENTS

| | | |
|---|---|---|
| 3,669,880 A | 6/1972 | Marantz |
| 3,776,819 A | 12/1973 | Williams |
| 3,850,835 A | 11/1974 | Marantz |
| 3,884,808 A | 5/1975 | Scott |
| 3,902,490 A | 9/1975 | Jacobsen et al. |
| 3,989,622 A * | 11/1976 | Marantz ............... A61M 1/1696 210/645 |
| 4,094,775 A | 6/1978 | Mueller |
| 4,206,054 A | 6/1980 | Moore |
| 4,209,392 A | 6/1980 | Wallace |
| 4,376,707 A | 3/1983 | Lehmann |
| 4,460,555 A | 7/1984 | Thompson |
| 4,581,141 A | 4/1986 | Ash |
| 4,650,587 A | 3/1987 | Polak |
| 4,684,460 A | 8/1987 | Issautier |
| 5,230,702 A | 7/1993 | Lindsay et al. |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Indriksons |
| 5,849,179 A | 12/1998 | Emerson et al. |
| 5,858,186 A | 1/1999 | Glass |
| 5,944,684 A | 8/1999 | Roberts |
| 6,036,858 A | 3/2000 | Carlsson |
| 6,114,176 A | 9/2000 | Edgson et al. |
| 6,126,831 A | 10/2000 | Goldau et al. |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,283 B2 | 4/2005 | Thompson |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor |
| 7,276,042 B2 | 10/2007 | Polaschegg |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,566,432 B2 | 7/2009 | Wong |
| 7,597,806 B2 | 10/2009 | Uchi |
| 7,794,419 B2 | 7/2010 | Paolini et al. |
| 7,776,210 B2 | 8/2010 | Rosenbaum |
| 7,850,635 B2 | 12/2010 | Polaschegg |
| 7,922,686 B2 | 4/2011 | Childers et al. |
| 7,922,911 B2 | 4/2011 | Micheli |
| 7,947,179 B2 | 5/2011 | Rosenbaum |
| 7,955,290 B2 | 6/2011 | Karoor et al. |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 11/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,187,250 B2 | 5/2012 | Roberts |
| 8,197,439 B2 | 6/2012 | Wang et al. |
| 8,303,532 B2 | 11/2012 | Hamada et al. |
| 8,404,491 B2 | 3/2013 | Ding et al. |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 9,144,640 B2 | 9/2015 | Pudil |
| 2001/0007931 A1 | 7/2001 | Blatter |
| 2002/0112609 A1 | 8/2002 | Wong |
| 2002/0117436 A1 | 8/2002 | Rajan |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2004/0019312 A1 | 1/2004 | Childers et al. |
| 2004/0099593 A1 | 5/2004 | DePaolis |
| 2004/0147900 A1 | 7/2004 | Polaschegg |
| 2004/0168963 A1 | 9/2004 | King |
| 2004/0257409 A1 * | 12/2004 | Cheok ................. B41J 2/17506 347/84 |
| 2005/0006296 A1 | 1/2005 | Sullivan |
| 2005/0113796 A1 | 5/2005 | Taylor |
| 2005/0150832 A1 | 7/2005 | Tsukamoto |
| 2005/0274658 A1 | 12/2005 | Rosenbaum |
| 2006/0037483 A1 * | 2/2006 | Kief, Jr. .............. A47J 31/4467 99/295 |
| 2006/0241543 A1 | 10/2006 | Gura |
| 2007/0007208 A1 | 1/2007 | Brugger et al. |
| 2007/0179431 A1 | 8/2007 | Roberts |
| 2007/0213665 A1 | 9/2007 | Curtin |
| 2008/0006570 A1 | 1/2008 | Gura |
| 2008/0051696 A1 | 2/2008 | Curtin |
| 2008/0053905 A9 | 3/2008 | Brugger et al. |
| 2008/0217245 A1 | 9/2008 | Rambod |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0157877 A1 | 6/2009 | Baek |
| 2009/0216045 A1 | 8/2009 | Singh |
| 2009/0266358 A1 | 10/2009 | Sacristan Rock |
| 2010/0004588 A1 | 1/2010 | Yeh |
| 2010/0007838 A1 | 1/2010 | Fujimoto |
| 2010/0078381 A1 | 4/2010 | Merchant |
| 2010/0084330 A1 | 4/2010 | Wong |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114012 A1 | 5/2010 | Sandford |
| 2010/0217181 A1 | 8/2010 | Roberts |
| 2010/0224492 A1 | 9/2010 | Ding et al. |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding et al. |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 * | 11/2011 | Braig .................... B01D 61/44 210/632 |
| 2011/0297593 A1 | 12/2011 | Kelly |
| 2012/0018377 A1 | 1/2012 | Tsukamoto |
| 2012/0248017 A1 | 10/2012 | Beiriger |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0190885 A1 | 7/2014 | Meyer |
| 2014/0190891 A1 | 7/2014 | Lura |

(56) References Cited

U.S. PATENT DOCUMENTS

| | | |
|---|---|---|
| 2014/0217028 A1 | 8/2014 | Pudil |
| 2014/0251908 A1 | 9/2014 | Ding |
| 2014/0276374 A1* | 9/2014 | Minkus ............... A61M 1/288 604/28 |
| 2014/0326671 A1 | 11/2014 | Kelly |
| 2015/0057602 A1 | 2/2015 | Mason |
| 2015/0108609 A1 | 4/2015 | Kushida |
| 2015/0114891 A1* | 4/2015 | Meyer ............... A61M 1/3465 210/85 |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |

FOREIGN PATENT DOCUMENTS

| | | |
|---|---|---|
| EP | 1592494 B1 | 6/2009 |
| EP | 2575827 A2 | 12/2010 |
| EP | 2576453 A2 | 12/2011 |
| EP | 1545652 B1 | 1/2013 |
| EP | 1345856 B1 | 3/2013 |
| EP | 2344220 B1 | 4/2013 |
| WO | 9532010 A1 | 11/1995 |
| WO | 0185295 A2 | 11/2001 |
| WO | 2002043859 | 6/2002 |
| WO | 2003043677 A2 | 5/2003 |
| WO | 2003051422 A2 | 6/2003 |
| WO | 2004064616 A2 | 8/2004 |
| WO | 2004062710 A3 | 10/2004 |
| WO | 2005123230 A2 | 12/2005 |
| WO | 2007089855 A2 | 8/2007 |
| WO | 2008075951 A1 | 6/2008 |
| WO | 2009157877 A1 | 12/2009 |
| WO | 2009157878 A1 | 12/2009 |
| WO | 2010028860 A1 | 3/2010 |
| WO | 2010102190 A4 | 11/2010 |
| WO | 2010141949 | 12/2010 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 | 2/2013 |
| WO | 2013028809 A3 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | 2015142624 | 9/2015 |
| WO | 2015199764 | 12/2015 |

OTHER PUBLICATIONS

PCT/US2015/032492 International Search Report dated Nov. 19, 2015.
PCT/US2015/016270 International Search Report and Written Opinion dated Jun. 5, 2015.
PCT/US2015/016273 International Search Report and Written Opinion dated Jun. 9, 2015.
PCT/US2015/032492 Written Opinion dated Nov. 19, 2015.
PCT Application, PCT/US20013/020404, filed Jan. 4, 2013.
PCT/US2015/020046 International Search Report and Written Opinion dated Jun. 29, 2015.
PCT/US2015/020044 International Search Report Written Opinion dated Jun. 30, 2015.
PCT/US15/18587 International Preliminary Report on Patentability Dated Jun. 6, 2016
European Search Report for App. No. 15751391.2 dated Aug. 4, 2017.
European Search Report and supplementary Search Report for App. No. 14865374.4 dated Jun. 12, 2017.
European Search Report for EP App. No. 15811573.3, dated Feb. 15, 2018.
European Search Report for EP App. No. 15810804.3, dated Feb. 15, 2018.
European Search Report for EP 15811439, dated Feb. 15, 2018.
PCT/US2015/019387 International Preliminary Report on Patentability dated Jun. 13, 2016.
PCT/US2015/019387 International Search Report and Written Opinion dated Jun. 12, 2015.
Office Action for Chinese Application No. 2015/80009562.5 dated Jul. 3, 2017.
International Preliminary Report on Patentability for Application No. PCT/US2015/032492 dated Jun. 30, 2017.
International Preliminary Report on Patentability for Application No. PCT/US2015/016273 dated Feb. 19, 2016.

* cited by examiner

UREASE INTRODUCTION SYSTEM FOR REPLENISHING UREASE IN A SORBENT CARTRIDGE

FIELD OF THE INVENTION

The invention relates to an apparatus and related methods for replenishing urease in a sorbent cartridge. The urease in the sorbent cartridge can be replenished by adding urease to a system via an injection port or compartment that can contains one or more modular urease pouches. The injection port site or compartment can be in fluid communication with the sorbent cartridge via a dialysis flow path, such that urease added to the flow path can travel to the sorbent cartridge where the urease can be immobilized by adsorption onto a urease-binding material such alumina or silica inside the sorbent cartridge. The urease-binding material can be optionally placed inside the sorbent cartridge permanently, thereby reducing cost, and simplifying the design and engineering of the system. Urease can be added as needed to replenish the system and recharge the urease-binding material with fresh urease before, during, or after a dialysis session. The sorbent cartridge can contain other sorbent materials that can also be recharged such as zirconium phosphate.

BACKGROUND

Urease is a water soluble enzyme used in dialysis to convert urea into ammonium ions and bicarbonate. Urease can be immobilized electrostatically, covalently, or by adsorption on an alumina or silica substrate inside a sorbent cartridge that is designed to be connected to a dialysis system. However, conventional immobilization of urease has been associated with the disadvantages of low loading and leaching of urease that can result in low urease sufficiency in dialysis. Moreover, conventional sorbent dialysis systems cannot replenish, i.e., provide additional or specified amounts of urease to the sorbent cartridge or dialysis system before, during, or after a dialysis session. The inability to control the amount of urease added or available for use can be problematic because the amount of urease required for a particular dialysis session can vary. The amount of urease required for a dialysis session may depend on a number of factors such as patient weight, urea load, dialysis time, etc. resulting in different rates and amounts of urease required per session. Using more or less than the required amount of urease for a particular dialysis session can translate into increased expenditures and waste from unused or overused sorbent materials.

Known sorbent dialysis cartridges and systems further cannot measure the amount of urease used during a particular session or replenish urease back to the sorbent cartridge or system as needed should a session need additional quantities of urease, or should additional urease be needed in the case of faster fluid flow rates through the sorbent cartridge.

Sometimes, certain sorbent materials such as alumina and zirconium phosphate can be recharged such that the sorbent material is put back into a condition for use in sorbent dialysis. Even though many systems contain rechargeable components, currently known systems cannot recharge some or all of the sorbent materials. The current problem has been that present sorbent cartridges contain urease, which makes recharging the system without losing the functional capacity of the urease difficult or nearly impossible. For example, recharging zirconium phosphate in the same sorbent cartridge in which urease is immobilized on alumina or silica can result in urease being stripped off the alumina or silica. Known systems cannot replenish urease lost due to the process of recharging other sorbent materials inside the same cartridge, or add a specific amount of urease to a sorbent cartridge or sorbent system.

The ability to manufacture, ship and store sorbent cartridges without urease pre-loaded can reduce costs and wastes. Urease has a limited shelf life, and so the ability to add urease just before a dialysis session reduces wastes associated with the degradation of urease during storage. Known systems cannot provide for a sorbent cartridge to be shipped and stored without pre-loaded urease with the urease being easily addable at a later time.

As such, there is a need for systems, methods, components and devices for optimizing use of sorbent materials such as urease within a sorbent cartridge. The need extends to systems that can replenish urease in a sorbent cartridge and related dialysis systems by either directly adding discrete amounts of urease or by continuously adding urease to the sorbent system by a delivery mechanism. The need includes a sorbent cartridge and related systems in which urease can be added on demand, continuously, and in specified, discrete amounts. The need extends to providing urease at a specified time such as after, before, or during a dialysis session. The need includes providing the urease while the system is operating or off-line. The need includes adding the desired amounts of urease in a simple and convenient manner and in adjustable amounts. In general, the need can be broadly described as dynamically adding urease to sorbent cartridges and related dialysis systems. The need can include adjusting the amount of required urease depending on a measured amount of ammonia detected anywhere in the system or sorbent cartridge.

There is also a need for a mechanism of directly adding urease to a sorbent cartridge, on demand. The need includes a way to inject urease into a sorbent cartridge or a part of a flow path anywhere upstream of the sorbent cartridge in the dialysis system by an easy-to-use delivery mechanism. There is also a need for a sorbent cartridge in which fresh urease can be added via a delivery mechanism to replenish or refill the urease in the sorbent cartridge. There is a need for the delivery mechanism that is conveniently located so that access the sorbent cartridge is unnecessary in order to replenish sorbent materials. There is also a need for measuring an amount of urease required to be dynamically added to a sorbent cartridge.

There is a need for a system that allows for a sorbent cartridge to be shipped or stored without pre-loaded urease. There is further a need for a fully rechargeable sorbent cartridge containing urease. There is also a need for a system capable of replenishing urease that may be stripped out of the sorbent cartridge during maintenance or during a dialysis session.

SUMMARY OF THE INVENTION

The first aspect of the invention relates to a dialysis flow loop. In any embodiment of the first aspect of the invention, the dialysis flow loop can comprise a sorbent cartridge containing a urease-binding sorbent material positioned on the flow loop, and a urease compartment positioned upstream of the sorbent cartridge and in fluid communication with the sorbent cartridge, wherein the urease compartment is adapted for receiving urease.

In any embodiment of the first aspect of the invention, the urease-binding sorbent material can be either alumina, silica, or a combination thereof, and the urease compartment can receive urease.

In any embodiment of the first aspect of the invention, the urease compartment can comprise a urease pump, wherein the urease pump is configured to direct fluid from the urease compartment into the dialysis flow loop.

In any embodiment of the first aspect of the invention, the dialysis flow loop can comprise a dialysis cabinet, wherein the dialysis flow loop is in an interior of the dialysis cabinet and the urease compartment is configured to open to an exterior side of the dialysis cabinet.

In any embodiment of the first aspect of the invention, the urease compartment can be slideably disposed on the dialysis cabinet, and the urease compartment can be hermetically sealed to the dialysis cabinet when the urease compartment is in a closed position.

In any embodiment of the first aspect of the invention, the urease compartment can be adapted to receive one or more of a urease pouch, solid urease, or a removable urease cartridge.

In any embodiment of the first aspect of the invention, the sorbent cartridge can comprise one or more sorbent materials selected from the group consisting of activated carbon, hydrous zirconium oxide, zirconium phosphate, and ion-exchange resin.

In any embodiment of the first aspect of the invention, at least one of the sorbent materials can be rechargeable.

In any embodiment of the first aspect of the invention, the dialysis flow loop can comprise one or more valves positioned between the urease compartment and the sorbent cartridge, wherein the one or more valves are configured to control the amount of fluid moving from the urease compartment to the sorbent cartridge.

Any of the features disclosed as being part of the first aspect of the invention can be included in the first aspect of the invention, either alone or in combination.

The second aspect of the invention is directed to a dialysis flow loop that can comprise a sorbent cartridge, wherein the sorbent cartridge contains a urease-binding sorbent material; and a urease injection port in fluid communication with the sorbent cartridge, wherein the urease injection port is positioned upstream of the sorbent cartridge, and wherein the urease injection port is adapted to receive a solution of urease.

In any embodiment of the second aspect of the invention, the dialysis flow loop can comprise a urease pump, wherein the urease pump is configured to move fluid from the urease injection port to the dialysis flow loop.

In any embodiment of the second aspect of the invention, the urease-binding sorbent material can be either alumina, silica, or a combination thereof, and the urease injection port can be adapted to receive a syringe.

In any embodiment of the second aspect of the invention, the sorbent cartridge can comprise one or more sorbent materials selected from the group consisting of activated carbon, hydrous zirconium oxide, zirconium phosphate, and ion-exchange resin.

In any embodiment of the second aspect of the invention, at least one of the sorbent materials can be rechargeable.

In any embodiment of the second aspect of the invention, the dialysis flow loop can comprise a urea detector positioned downstream of the alumina or silica.

Any of the features disclosed as being part of the second aspect of the invention can be included in the second aspect of the invention, either alone or in combination.

The third aspect of the invention is related to a method of replenishing urease in a sorbent cartridge. In any embodiment of the third aspect of the invention, the method can comprise the step of injecting a urease solution into a urease injection port, wherein the urease injection port is in fluid communication with the sorbent cartridge, and wherein the urease injection port is positioned upstream of the sorbent cartridge.

In any embodiment of the third aspect of the invention, the method can comprise controlling a urease pump to pump the urease solution into the sorbent cartridge.

In any embodiment of the third aspect of the invention, the method can comprise determining an amount of urease in the sorbent cartridge by sensing the presence of one or more solutes in a fluid downstream of the sorbent cartridge, and injecting the urease solution if the amount of urease in the sorbent cartridge is below a pre-set level.

In any embodiment of the third aspect of the invention, the injection can automatically be performed by a dialysis system.

In any embodiment of the third aspect of the invention, the injection can be performed during a dialysis session.

In any embodiment of the third aspect of the invention, the dialysis flow loop can comprise a urea detector positioned downstream of the urease-binding sorbent material.

Any of the features disclosed as being part of the third aspect of the invention can be included in the third aspect of the invention, either alone or in combination.

The fourth aspect of the invention relates to a method of replenishing urease in a sorbent cartridge comprising the steps of introducing urease into a urease compartment, wherein the urease compartment is in fluid communication with the sorbent cartridge, introducing fluid to the urease compartment to dissolve the urease, and introducing the fluid having the dissolved urease to the sorbent cartridge.

In any embodiment of the fourth aspect of the invention, the method can comprise introducing any one of a solid urease, a removable urease cartridge, and a urease pouch to the urease compartment.

In any embodiment of the fourth aspect of the invention, the method can further comprise the step of using one or more pumps to add fluid to the urease compartment to introduce the fluid having the dissolved urease to the sorbent cartridge.

Any of the features disclosed as being part of the fourth aspect of the invention can be included in the fourth aspect of the invention, either alone or in combination.

DETAILED DESCRIPTION OF THE INVENTION

Figure 1:
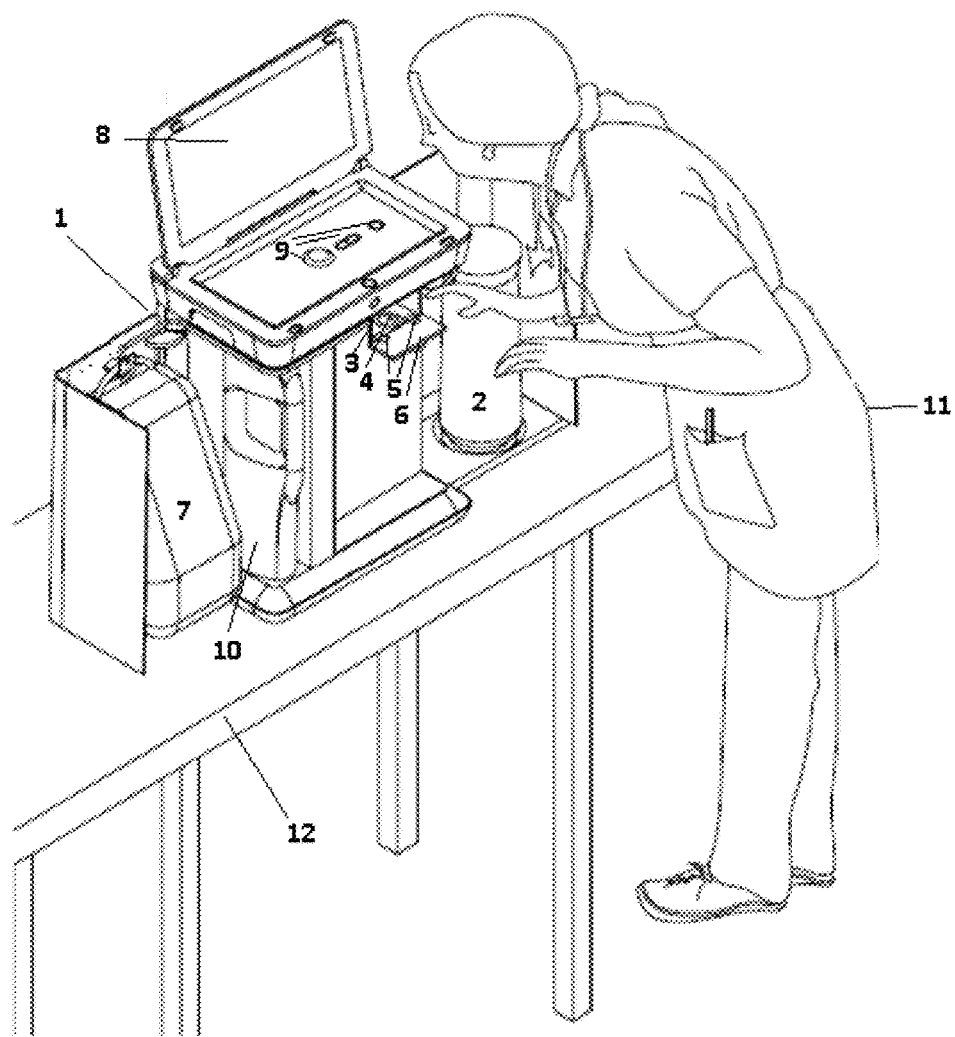
FIG. 1 is a perspective view of a dialysis cabinet having a urease compartment for addition of a urease pouch.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "adapted to receive" refers to a component wherein introduction of a substance into the component is possible.

An "adjustable amount" refers to an amount of a sorbent material that can be, but is not required to be, changed during a dialysis session.

An "ammonium sensor" is a sensor that is capable of detecting the presence of, or concentration of ammonium, ammonia, or ammonium ions.

The term "appropriate amount of solutes" refers to an amount of one or more solute(s) that is sufficient to accomplish a particular task. For example, an "appropriate amount of solutes" necessary to recharge the zirconium phosphate in a sorbent cartridge is the amount of sodium and hydrogen necessary to recharge the zirconium phosphate. The appropriate amount can be greater than the minimum amount necessary to accomplish the particular task.

A "blood urea nitrogen assay" is any analytical test that can determine the concentration of urea in blood or other fluids.

The term "cartridge" refers to any container designed to contain a powder, fluid, or gas made for ready connection to a device, structure, system, flow path or mechanism. The container can have one or more compartments. Instead of compartments, the container can also be comprised of a system of two or more modules connected together to form the cartridge wherein the two or more modules once formed can be connected to a device, structure, system, flow path or mechanism.

A "chemical sensor" is a sensor that senses one or more variables based on the chemical properties of a component of a medium.

A "compartment" means a part or a space designated, defined, marked or partitioned off from a structure. For example, a urease compartment in a sorbent cartridge is space defined within the sorbent cartridge containing urease. Optionally, the compartment can be in selected fluid communication with other compartments or modules of the sorbent system. The compartment can be physically separated or marked off without a physical barrier.

A "component" is any portion of a larger system. Non-limiting examples of components are containers, reservoirs, sensors, modules, and sorbents.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "contain" as used herein means to keep a material within a specific place. "Contain" can refer to materials that are placed within a compartment, absorbed onto a component, bound to a component, or any other method of keeping the material in a specific place.

The term "container" as used herein is a receptacle that may be flexible or inflexible for holding any fluid or solid, such as for example a spent dialysate fluid, or a sodium chloride or sodium bicarbonate solution or solid, or urease, or urease/alumina, and the like. Generally, a container is a component of a larger system. A "sorbent container" is any receptacle configured to hold one or more sorbent materials. Similarly, a "urease container" is any receptacle configured to hold urease.

"Cooperatively engaging" describes two compartments that have complementary engagement members that allow for an engagement configuration. "Dialysate" is the fluid that passes through the dialyzer membrane.

"Dialysis" is a type of filtration, or a process of selective diffusion through a membrane. Dialysis removes solutes in the blood of a specific range of molecular weights via diffusion through a membrane from a fluid to be dialyzed. During dialysis, a fluid to be dialyzed is passed on one side of a filter membrane, while dialysate is passed on the other side of that membrane. Dissolved solutes are transported across the filter membrane by diffusion between the fluids. The dialysate is used to remove solutes from the blood being dialyzed. The dialysate can also provide enrichment to the other fluid.

A "dialysis cabinet" is a structure configured to contain the modules, flow loops and other components necessary for dialysis. A "dialysis cabinet," in some embodiments, can be more than one structure designed to be used in combination for dialysis. Not all necessary components need to be in the dialysis cabinet, and a dialysis cabinet can contain components that are not strictly necessary for dialysis.

A "dialysis flow path" is the route in which a fluid will travel during dialysis.

A "dialysis session" refers to the medical procedure wherein dialysis is performed on a patient.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Engagement members" allow compartments to cooperatively engage. In certain embodiments, these engagement members may be clasps or latches.

An "exterior" or "exterior side" is a portion of a container or component that is on the outside of the container or component, as opposed to an "interior section" of a container or component, which denotes the inside of the container or component.

"Flow" refers to the movement of a fluid or gas.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

The term "fluidly connectable" refers to the ability of providing for the passage of fluid or gas from one point to another point. The two points can be within or between any one or more of compartments, modules, systems, components, and rechargers, all of any type.

"Functional capacity" is the ability of a material to accomplish the material's intended function. In some instances functional capacity can refer to the ability of a sorbent material to remove specific solutes from a fluid, or to transform specific solutes into other materials.

"Hermetically sealed" refers to a seal that is airtight, or substantially impermeable to gases or fluids.

"Hingeably disposed" refers to a method of attachment wherein one component is connected to a second component by a hinge. The hinge allows for one component to turn or pivot while the other component is stationary.

"Immobilized," as used to refer to a chemical component, refers to a configuration wherein a chemical component is held in place by some force. The force may be provided by absorption, adsorption, adhesion, or any other method for the chemical to be held in place.

"Module" or "modular" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. The designation of "first," "second," "third," etc. does not refer to the respective placement of the module in the direction of fluid or gas flow, but merely serves to distinguish one module from another unless otherwise indicated.

An "open" position is a configuration wherein the interior of a component is exposed to the surroundings. A "closed" position is a configuration wherein the interior of the component is cut off from the surroundings by a wall or other separator.

An "optical sensor" is a sensor that senses one or more variables based on changes in the light emitted from, reflected from, absorbed by, or that travels through a medium.

The terms "pathway," "conveyance pathway," "fluid flow path," and "flow path" refer to the route through which a fluid or gas, such as dialysate or blood, travels.

"Recharging" refers to the process of treating a sorbent material to restore the functional capacity of the sorbent material, so as to put the sorbent material back into a condition for reuse or for use in a new dialysis session. In some instances, the total mass, weight and/or amount of "rechargeable" sorbent materials remain the same. In other embodiments, the total mass, weight and/or amount of "rechargeable" sorbent materials may change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a particular sorbent material such as urease. Notably, urease is not generally "recharged," but can be replenished, as defined herein.

"Replenishing" means to add back into a system, section or module, a material that was previously removed, reduced, depleted, or taken out from that system, section or module. For example, after introducing an amount of a sorbent material, e.g., urease, that was reduced in quantity and/or functional capacity in a compartment, the compartment with the freshly introduced sorbent material can then be said to be "replenished."

"Reusable" refers in one instance to a material that can be used more than one time, possibly with treatment or recharging of the material between uses. Reusable may also refer to a cartridge that contains a material that can be recharged by recharging the material(s) contained within the cartridge.

A "section" refers to any portion of a larger component. A section can be referred to as a "first section," "second section," "third section," etc. to refer to any number of sections. The designation of "first," "second," "third," etc. does not refer to the respective placement of the section in the direction of fluid or gas flow, but merely serves to distinguish one section from another unless otherwise indicated. Additionally, each section can be optionally physically separated such as by a divider or wall; however, referring to a particular section does not necessarily require physical separation and can merely refer to a particular location in which a material is contained.

A "sensor" is a component capable of determining the states of one or more variables in a system. In one embodiment, a sensor may be capable of sensing the presence and/or concentration of at least one compound in the fluid flowing through at least one urease pouch, using any means known in the art.

"Solid urease" refers to urease in the solid phase of matter. The solid urease can be in a block of solid urease or in powdered form.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular dialysate regeneration assembly wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

"Sorbent materials" are materials capable of removing specific solutes from solution, such as urea or urea byproducts.

"Spent dialysate" is a dialysate contacted with blood through a dialysis membrane and contains one or more impurities, or waste species, or waste substances, such as urea.

"Upstream" of a section means positioned prior to that section in a fluid flow path. In normal operation, fluid will pass the "upstream" portion before passing the "downstream" portion.

The term "urease-binding sorbent material" refers to any material that can bind urease via any means including electrostatic, enzymatic, or intermolecular force binding of any kind.

A "urease cartridge" is a container designed to contain an amount of urease and connect into a dialysis system such that fluid can enter the urease cartridge, dissolve the urease, and exit the urease cartridge.

The term "urease compartment" or "urease container" refers to a defined space or partition of any kind made from any material adapted for containing urease.

The term "urease door," or "door," refers to a portion of a component such as a sorbent cartridge that can be opened, and the contents of the sorbent cartridge behind the door can optionally be replaced.

The terms "urease injection port" or "injection port" refer to a temporary or non-temporary opening or passageway allowing for the entry of urease from one compartment to another.

A "urease pouch" refers to a structure that contains at least urease, and optionally one or more other sorbent material, and is constructed from a material that can allow fluid to freely pass through the urease pouch while keeping undissolved urease inside. In some embodiments, a urease pouch can allow dissolved urease to pass out of the urease pouch.

A "urea sensor" is a component capable of detecting the presence of, or concentration of urea in a fluid.

The term "urease solution" refers to any aqueous solution being formulated by blending a solvent, such as a water based solvent, and urease. The solution can have optional components such as buffering components.

"Uremic toxins" are toxins carried in the blood supply normally removed in the kidneys.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

The terms "waste species," "waste products," "waste," or "impurity species" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

Urease Replenishment System

The present invention provides for a sorbent cartridge containing all non-water soluble, rechargeable components inside at least one compartment within, or contained separate from, the sorbent cartridge. In any embodiment of the first through fourth aspects of the invention, one or more of the sorbent materials can be rechargeable as described herein. The single compartment design contemplated by the invention can reduce fabrication and maintenance costs. During use, the non-water soluble, rechargeable components such as alumina and zirconium phosphate can be recharged. Any urease that is stripped off or required for operation can be added in a subsequent step back into the sorbent cartridge by the system or user. In this manner, the urease binding material such as alumina or silica in the sorbent cartridge can be replenished with urease. The sorbent cartridge of the present invention includes re-filling or re-supplying, or otherwise adding an amount of the replenishable sorbent material, such as urease, back into the sorbent cartridge and related systems. Replenishing the sorbent cartridge can be done at any time before, during, or after a dialysis session. As provided herein, the recharging of sorbent materials, such as alumina or zirconium phosphate, describes the ability to restore or enhance the functional capacity of the material. For example, alumina or zirconium phosphate can be recharged and restored to functional capacity by passing a solution containing the appropriate amount of solutes over the alumina or zirconium phosphate during a recharging process. Similarly, a rechargeable section or module can be recharged by passing the necessary solution through the section or module to restore the functional capacity of the module or section. In contrast, a replenishable sorbent material, in which the functional capacity has been reduced, is required to be replenished as described herein. Urease can be adsorbed by alumina, silica, or by combinations thereof wherein any such composition is rechargeable as defined herein.

The first through fourth aspects of the invention also allow for the sorbent cartridge to be stored and shipped without the need to pre-load the sorbent cartridge with urease. The system of the present invention allows a user to simply add urease in an external addition location to load the urease into the sorbent cartridge. In addition to introducing urease to a sorbent cartridge, the first through fourth aspects of the invention further allow an introduction of an amount of urease solution into any fluid flow path of a dialysis system. The fluid flow path can be appurtenant to an entry or inlet of a sorbent cartridge. The fluid flow path can also be any particular defined direction of fluid inside the sorbent cartridge. The urease solution can travel through the fluid flow path until the urease contacts a urease-binding sorbent material, such as alumina, silica, or combinations thereof, in a sorbent cartridge. The urease can then be adsorbed by the alumina, silica, and combinations, where the urease can stay for the duration of dialysis. The urease can also be immobilized or bound by any known means or material known by those of ordinary skill such as electrostatic or enzymatic binding. The urease can further be bound by any intermolecular interaction such as van der Waals forces or by adsorption. By adding fresh urease in this fashion, urease can be added to either open or closed sorbent systems. Further, the system can be used with a reusable sorbent cartridge. By providing urease via a urease injection port or compartment, the sorbent cartridge can be shipped or stored without the urease present, while the urease can be added prior to, during, or after the sorbent cartridge is used. The fact that an adjustable amount of urease can be introduced can reduce costs associated with the complexity and timing of manufacturing a sorbent cartridge containing urease. Notably, depending on such factors as the formulation and the storage state of the urease, the urease may have a limited shelf life. Moreover, the sorbent cartridge can be stored for long periods of time without problems to the viability of the urease by injecting the urease just prior to starting dialysis.

In particular, a sorbent cartridge can be replenished with fresh urease for each dialysis session wherein replenishing the urease in the sorbent cartridge can result in the recharging of other sorbent materials in the sorbent cartridge. For example, an alumina, silica substrate, or combinations thereof, which bind urease, in the sorbent cartridge, can be "recharged" and then replenished with urease. Thereby, a single cartridge design with all components can be provided to simplify design and reduce cost per session.

One non-limiting embodiment of a dialysis system of the first through fourth aspects of the invention, with a urease introduction system is shown in FIG. 1. The dialysis system can be housed within a dialysis cabinet 1 shown on table 12. A sorbent cartridge 2 can be housed within the dialysis cabinet 1 in a dialysis flow loop. Spent dialysate, containing impurities such as urea, travels through the sorbent cartridge where the impurities are removed for dialysate regeneration. Dialysate regeneration refers to the process of treating spent dialysate, containing solutes removed from the patient's blood, with one or more sorbent materials in order to remove specific solutes, such as urea, and thereby generate dialysate that can be reused for dialysis. The resulting dialysate travels back to the dialyzer (not shown) where further impurities from the patient's blood can pass through the semi-permeable membrane and into the dialysate.

In any embodiment of the first through fourth aspects of the invention, the dialysis cabinet 1 can comprise a urease compartment 3. In any embodiment of the first through fourth aspects of the invention, the urease compartment 3 can be slideably removable from the dialysis cabinet 1. In any embodiment of the first through fourth aspects of the invention, the urease compartment 3 can be opened by cover 6, and need not be slideably removable from the dialysis cabinet 1. The cover 6 of the urease compartment 3 can be hingeably disposed on the dialysis cabinet 1 by hinges 5 as described herein. In any embodiment of the first through fourth aspects of the invention, the urease compartment 3 can be adapted to receive a urease pouch or solid urease. The size and shape of the urease compartment 3 can be such that one or more urease pouches can be placed within the urease compartment, or solid urease can be loaded into the urease compartment. Before, during, or after a dialysis session, or whenever the amount of urease is reduced, the user 11 can add a urease pouch 4 or solid urease into the urease compartment 3. The cover 6 of the urease compartment 3 can then be shut into the dialysis cabinet 1. The urease can be contained in a urease pouch 4 as described herein and shown in FIG. 1, or the urease can be in the form of solid urease.

The functional amount of the urease may be reduced in several ways: (1) the functional amount of urease may be reduced if the urease is stripped off of the sorbent cartridge due to the recharging of other sorbent materials, (2) by leaching out during dialysis, or during maintenance of the sorbent cartridge, or (3) by modification or rearrangement of the urease structure to make the urease less active.

In any embodiment of the first through fourth aspects of the invention, the urease compartment 3 can be hermetically sealed to prevent contamination or leaking when closed. The hermetic seal can be created with the use of PTFE sealing rings, o-rings, grease or any other material known in the art capable of creating a hermetic seal disposed on the edges of cover 6 and dialysis cabinet 1.

In any embodiment of the first through fourth aspects of the invention, the cover 6 may be hingeably disposed on the urease compartment 3, connected by a hinges 5. The hinges 5 can attach the cover 6 to the dialysis cabinet 1 by any means known in the art. In any embodiment of the first through fourth aspects of the invention, the hinge can be a butt hinge. A butt hinge comprises two rectangular leafs joined by a pin. One of the leaves can attach to the interior side of the cabinet and the other to the interior side of the cover. The hinge allows closing, wherein the two leaves are moved together, pivoting on the pin to shut the cover.

In any embodiment of the first through fourth aspects of the invention, the hinge can be a living hinge instead of a separate hinge assembly. A living hinge is a hinge made out of, and often made integral with, the components that the hinge attaches. For example, the cover 6 may be made out of molded plastic. The living hinge can be a thinner piece of molded plastic integral with the cover 6. The living hinge can also attach to the dialysis cabinet 1 by any means known in the art, such as with screws, bolts or any other means for connection. The molded plastic of the living hinge can bend to allow movement of the cover and opening of the urease compartment. In any embodiment of the first through fourth aspects of the invention, the living hinge can be made out of a polymer such as polyethylene or polypropylene. The living hinge need not be made integral with the cover, and in any embodiment of the first through fourth aspects of the invention, may instead attach to the cover in any known fashion.

In any embodiment of the first through fourth aspects of the invention, engagement members (not shown) can be placed on the cover 6 of the urease compartment 3 and on the dialysis cabinet 1 to allow for sealing of the cover 3. When the engagement members on the cover 6 cooperatively engage with the engagement members on the dialysis cabinet 1, the cover 6 can be kept shut, and only opened when the engagement members are caused to disengage.

Once the urease compartment 3 is closed, the system can direct fluid from water reservoir 7 into the urease compartment 3, dissolving the urease. In any embodiment of the first through fourth aspects of the invention, water source 10 can be used to fill the water reservoir 7. In any embodiment of the first through fourth aspects of the invention, the water source 10 can be used to direct fluid into the urease compartment 3 directly, without the need for water reservoir 7. In any embodiment of the first through fourth aspects of the invention, a buffer solution can be used to dissolve the urease. Acid and base can be added to the water before the urease is dissolved, or a buffer solution can be kept in a reservoir (not shown) that can be used to provide buffer for dissolving the urease. In any embodiment of the first through fourth aspects of the invention, a priming solution or dialysate can be used for dissolving the urease as explained herein. The invention is adaptable to a wide range of fluids. The fluid, containing dissolved urease, can then be directed into the sorbent cartridge 2 where the urease can be immobilized on alumina or silica and combinations thereof, within the sorbent cartridge 2. The fluid connections between the urease compartment 3 and the sorbent cartridge 2 are described herein.

In any embodiment of the first through fourth aspects of the invention, the urease pouch 4 can be dissolvable in a suitable fluid. In such embodiments of the first through fourth aspects of the invention, the need to remove the urease pouch 4 after the addition of urease is eliminated. In any embodiment of the first through fourth aspects of the invention, wherein the urease pouch 4 is not water soluble, the user 11 can simply re-open the urease compartment 3 and remove the empty urease pouch. Non-limiting examples of dissolvable materials that can be used for the urease pouch include polyvinyl alcohols, thermoplastic fibers, or any other water soluble material capable of containing urease. In any embodiment of the first through fourth aspects of the invention, the urease pouch can be non-water soluble. After addition of urease, the urease pouch can be removed from the urease compartment, and optionally replaced with a new urease pouch.

In FIG. 1, the urease compartment 3 is shown at the top of the dialysis cabinet 1. The urease compartment 3 of the present invention can be located at any place on the interior or exterior of the dialysis cabinet 1 and is not limited to any particular place. In any embodiment of the first through fourth aspects of the invention, the urease compartment 3 can be located on the inside of the dialysis cabinet, and in any embodiment of the first through fourth aspects of the invention, the urease compartment 3 can be located on the exterior of the dialysis cabinet.

In any embodiment of the first through fourth aspects of the invention, the amount of urease added to the system can be determined based on the patient's weight and/or blood urea nitrogen (BUN). Patients with a higher BUN, or larger patients, may require more urease during a dialysis session. Because urease can be added to the sorbent cartridge prior to each dialysis session, a larger urease pouch, or multiple urease pouches, can be added for patients that may require additional urease. In any embodiment of the first through fourth aspects of the invention, the amount of urease can be added via a large, multi-session reservoir containing urease in connection with the machine. The large, multi-session reservoir can contain amounts of urease sufficient for a plurality of dialysis session or even amounts sufficient for dialysis sessions spanning days, weeks, or longer depending on the usage of the system. The large, multi-session reservoir can be integral to the dialysis system or can be a stand-alone component that is mated to the system to provide a connection when needed. The urease in the large, multi-session reservoir can be provided in solid, powdered or liquid form. The amount of urease provided by the large, multi-session reservoir can be selectively metered at an amount required for a particular session by an operator or by control components. In any embodiment of the first through fourth aspects of the invention, the metering processing can be automated using a computer, control systems, and related components such as motors, pumps, actuators, and the like, to reduce operator error and improve usability, safety, reliability, consistency of the system.

In any embodiment of the first through fourth aspects of the invention, additional reservoirs, lines and pumps can be added to the dialysis cabinet, including an infusate system, ultrafiltrate reservoir, or any other components known in the art for use with a dialysis system.

Console 8, shown in FIG. 1, can be used to provide messages or alerts to the user 11 or to set dialysis parameters for the dialysis session. User interface inputs 9 can be utilized by the user 11 to input information into the system. Such information can include whether a urease pouch 4 has been loaded, the amount of urease being added, or to direct the system to begin the urease replenishment process.

In any embodiment of the first through fourth aspects of the invention, a user can place a large amount of urease powder into urease compartment 3. The urease compartment 3 can provide a bulk powder supply having enough urease for several dialysis sessions, with the dialysis system being capable of dispensing urease from the bulk powder supply for each session. As necessary, the system can automatically meter some of the powder into a separate mixing chamber (not shown) using the control systems and related components described herein, where the metered amount of powder can be dissolved by water or other fluid and directed into the sorbent cartridge 2. The user can add a set amount of urease powder to the urease compartment 3. The system can then automatically move the appropriate amount of the urease powder to the mixing chamber when necessary for addition to the sorbent cartridge. This embodiment of the first through fourth aspects of the invention would allow the user to add larger amounts of solid urease into the dialysis cabinet 1 but only periodically. The system can then automatically meter the correct amount of powder into the mixing chamber (not shown) and control the urease addition. In any embodiment of the first through fourth aspects of the invention, a second, smaller reservoir can be used to added smaller amounts of urease specific for adding dialysis component during a session. One possible advantage of having a large, multi-session reservoir and a smaller, single-session reservoir is to provide flexibility wherein the a large, set amount of urease is made available for multi-session use, but smaller amounts of urease or other dialysis solutes can be added on a per-session basis as feedback is received.

Figure 2:
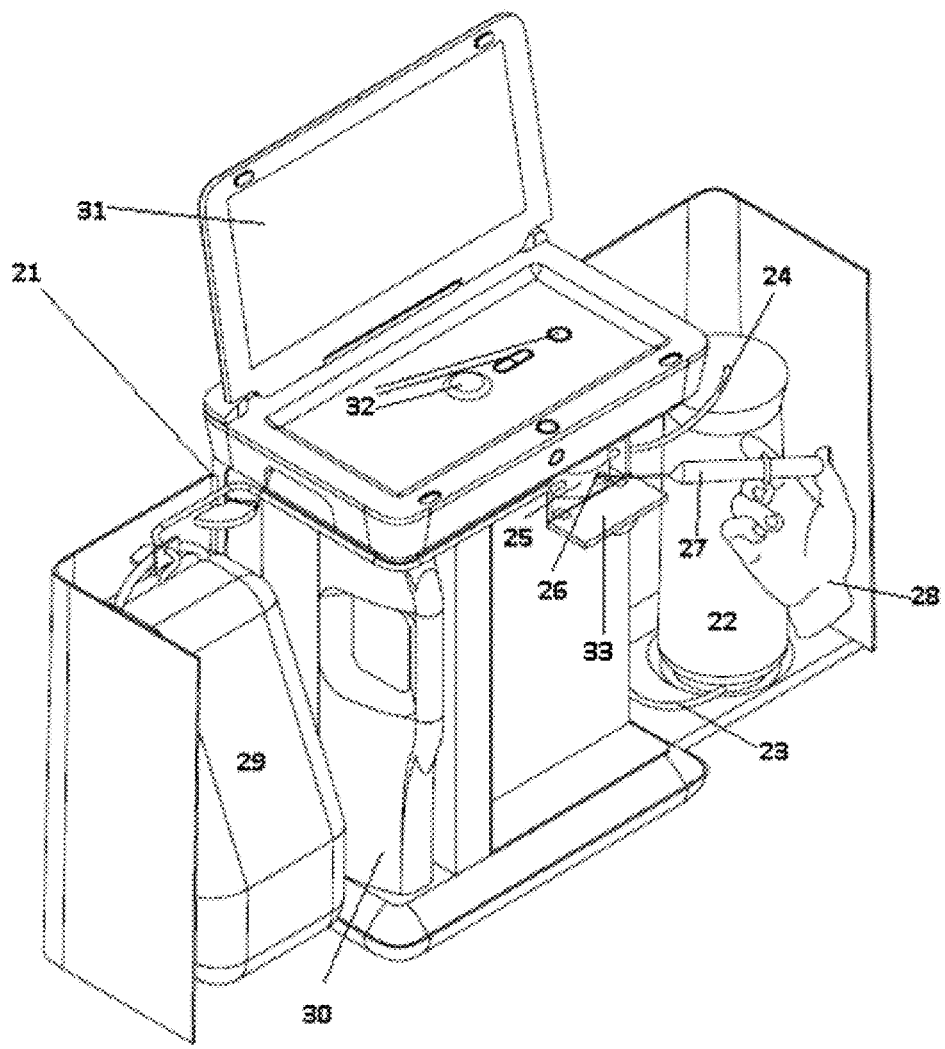
FIG. 2 is a perspective view of a dialysis cabinet with a urease injection port for injection of urease into the system located at the top of the dialysis cabinet.

FIG. 2 shows a second, non-limiting embodiment of the first through fourth aspects of the invention. Similar to FIG. 1, a dialysis cabinet 21 can house a dialysis system. The dialysis system can include a sorbent cartridge 22 with an inlet 23 and outlet 24. An injection port 25 can be disposed on the dialysis cabinet 21. In any embodiment of the first through fourth aspects of the invention, the injection port 25 can be located behind an optional door 33 to protect the injection port 25. The injection port 25 can be placed at any location on the interior or exterior of the dialysis cabinet 21. A solution of urease can be added to the system, such as by a syringe 27 inserted into the injection port 25 by user 28 through septum 26. The urease solution, once injected, can travel to the sorbent cartridge 22 where the urease can be immobilized by adsorption onto alumina or silica, and combinations thereof, within the sorbent cartridge 22. In any embodiment of the first through fourth aspects of the invention, the urease solution can be added before, during, or after a dialysis session, or whenever the amount of the urease is reduced. The user can inject an adjustable amount of urease into the system, allowing for a customizable sorbent system as described herein.

In any embodiment of the first through fourth aspects of the invention, the injection port 25 can be fluidly connected to a reservoir (not shown). The reservoir can be fluidly connected to the sorbent cartridge 22. After injection of the urease, the urease can be stored in reservoir. In order to replenish the urease in the sorbent cartridge, the user 28 can direct the system to pump the urease in the reservoir into the sorbent cartridge 22, where the urease can be adsorbed by the alumina or silica. In any embodiment of the first through fourth aspects of the invention, the system can automatically pump the urease into the sorbent cartridge 22 in response to a signal from a urea sensor (not shown) that shows an insufficient or inadequate amount of urease in the sorbent cartridge. In any embodiment of the first through fourth aspects of the invention, the system can notify the user of an insufficient amount of urease by an audio or visual signal on console 31, and the user can direct the pumping of urease into the sorbent cartridge, such as by using inputs 32. The inadequacy or insufficiency of urease can be determined by urea sensing wherein a computer processor processes a set of sensed inputs related to urease levels and makes a determination on an amount of urease to be added back into the system. In any embodiment of the first through fourth aspects of the invention, the reservoir does not need to be included. Instead, the injection port 25 can be directly connected into a line 23 fluidly connected to the sorbent cartridge 22.

In any embodiment of the first through fourth aspects of the invention, water reservoir 29 can be used to add water to the urease solution after injection. This can ensure that all of the injected urease has been flushed out of the injection port 25 and into the sorbent cartridge 22, and can also ensure that the injection port 25 is clean for the next urease injection. In any embodiment of the first through fourth aspects of the invention, water source 30 can supply the water to water reservoir 29. In any embodiment of the first through fourth aspects of the invention, the injected solution can contain a buffer and/or other excipients. In any embodiment of the first through fourth aspects of the invention, dialysate or priming solution can be directed through the injection port 25 as explained herein in order to flush out the injection port 25.

Figure 3:
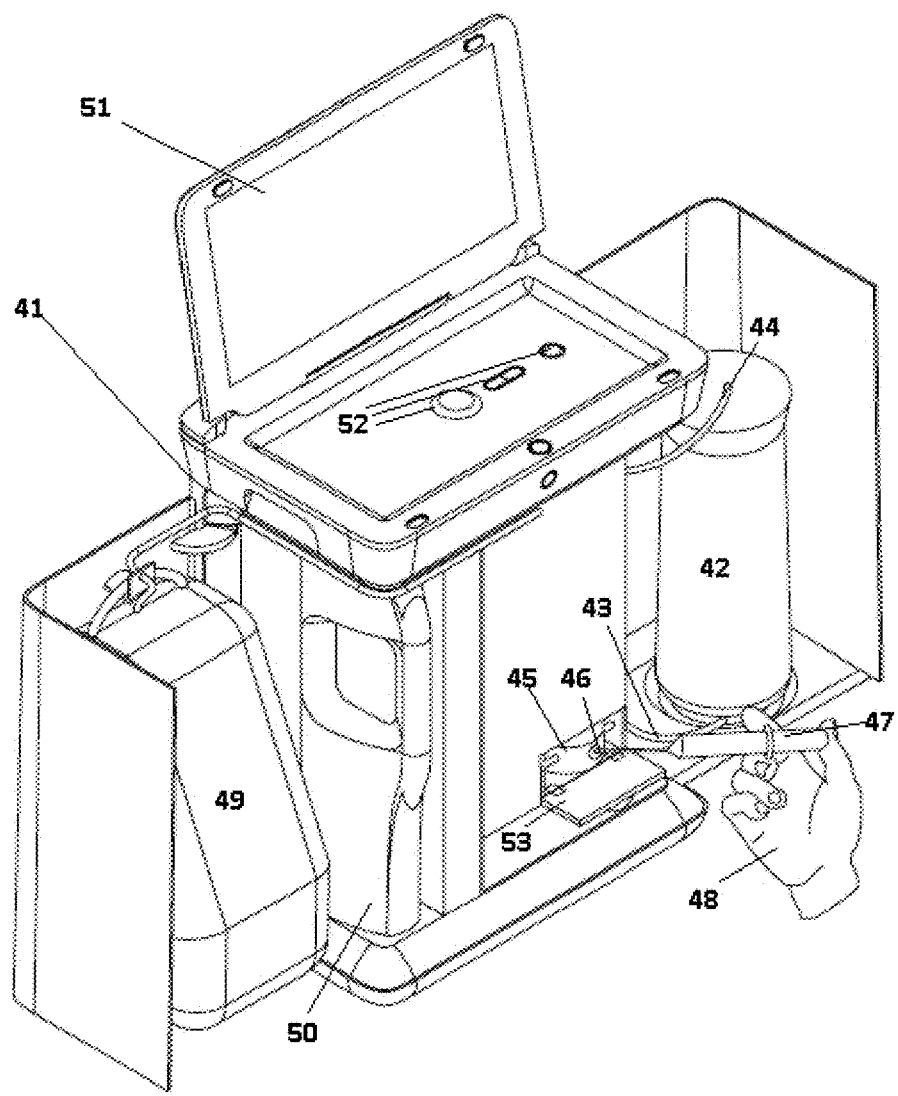
FIG. 3 is a perspective view of a dialysis cabinet with a urease injection port for injection of urease into the system located at the bottom of the dialysis cabinet.

The injection port can be located at any position on the interior or exterior of the dialysis cabinet that will allow for fluid communication with the sorbent cartridge. In FIG. 3 the urease injection port 45 is located behind optional door 53 at the bottom of the dialysis cabinet 41. The urease injection port 45 can still be fluidly connected to the sorbent cartridge 42 through inlet line 43. Outlet line 44 can connect the sorbent cartridge 42 to the rest of the dialysis flow path. As with the system shown in FIG. 2, the injection port 45 of FIG. 3 can have a pierceable septum 46. The user 48 can inject a urease solution with syringe 47 into the injection port 45 through septum 46. The urease, once injected into injection port 45 can flow through inlet connector 43 and into the sorbent cartridge 42. Water from water reservoir 49 can, in any embodiment of the first through fourth aspects of the invention, be used to flush the urease injection port 45. Water source 50 can be used to fill the water reservoir 49 and provide water for the dialysis session. Alternatively, the water source can contain optionally a buffer and/or an additional excipient. In any embodiment of the first through fourth aspects of the invention, a priming solution or dialysate can be used to flush the urease injection port 45. The addition of urease can be controlled through user interface 51, with the user inputting necessary information with inputs 52.

Any usable concentration of urease within the urease solution to be added via the injection port is within the scope of this invention. In any embodiment of the first through fourth aspects of the invention, the urease concentration can be between 10 mg/mL and 100 mg/mL. In any embodiment of the first through fourth aspects of the invention, the urease concentration can be between any of 1 mg/mL to 250 mg/mL, 15 mg/mL to 150 mg/mL, 10 mg/mL to 100 mg/mL, or 75 mg/mL to 250 mg/mL.

In any embodiment of the first through fourth aspects of the invention, the urease solution to be added can be provided in a pre-packaged amount. Before a dialysis session, whenever the amount of urease within the urease module or urease pouch is reduced, or after recharging the other sorbent materials, between 1.3 mL and 13.3 mL of urease solution can be added to ensure a fresh supply of urease within the sorbent cartridge. In any embodiment of the first through fourth aspects of the invention, the amount of urease solution added can be between any of 1.5 mL to 3.5 mL, 2.3 mL to 10.3 mL, or 5.0 mL to 12.3 mL, or more of urease solution with an activity of 300 unit/mg. In order to make use of the sorbent cartridge easier, and to enable use by non-trained users, such as patients, the urease can be provided in a separate sorbent container which contains the proper amount of urease to be added. A separate sorbent container containing a urease solution can ensure that the correct amount of urease is added to the sorbent cartridge, while avoiding waste by adding too much urease. In any embodiment of the first through fourth aspects of the invention, the amount of urease to be added can be based upon the needs of the patient. The amount of urease necessary for a dialysis session can depend on the blood urea nitrogen (BUN) content of the patient's blood. More urease can be added for patients with a higher BUN than for patients with a lower BUN. Heavier patients may also need more urease than patients that are lighter.

In any embodiment of the first through fourth aspects of the invention utilizing a urease injection port, any method of injecting the urease solution into the urease injection port is contemplated by this invention. For example, a user may fill a syringe with the urease solution and discharge the syringe into the injection port. The urease injection port may be covered by a septum, which can be pierced by the syringe. One of ordinary skill will appreciate that many types of injection ports can be used for the intended purpose of injecting urease. In any embodiment of the first through fourth aspects of the invention, the urease solution can simply be transferred by any suitable means into the urease injection port, and then pumped into the rest of the dialysis system using a system of pumps and actuators. In such embodiments of the first through fourth aspects of the invention, the urease injection port may be covered with a removable cap that can be removed prior to addition of the urease solution. In any embodiment of the first through fourth aspects of the invention, the dialysis machine (not shown) can automatically inject the urease into the injection port. A urease solution can be provided for within the dialysis machine. After the other sorbent materials within the sorbent cartridge are recharged, or whenever the amount of the urease is reduced, the machine can automatically inject fresh urease into the urease injection port. In any embodiment of the first through fourth aspects of the invention, the dialysis cabinet can meter in the correct amount of urease that is to be injected into the urease injection port.

Figure 4:
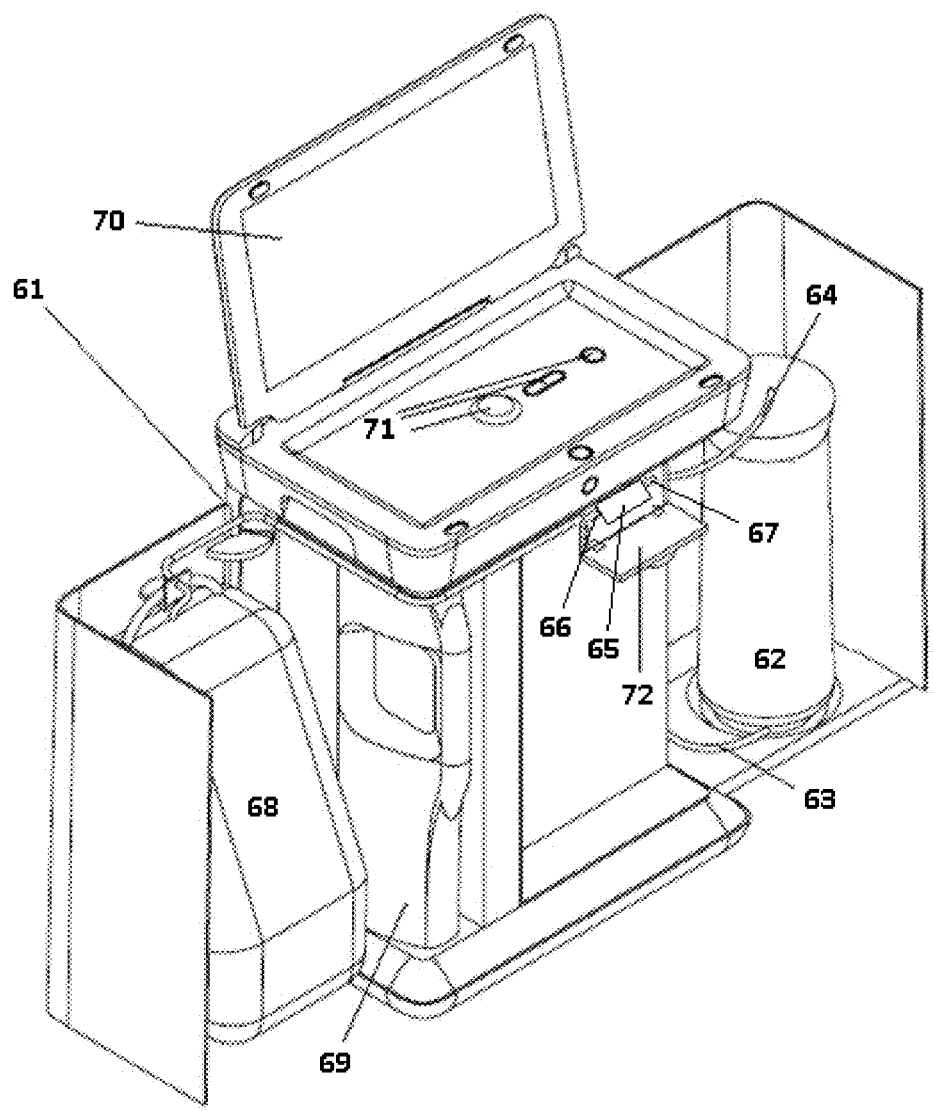
FIG. 4 is a perspective view of a dialysis cabinet with a removable urease cartridge.

FIG. 4 shows an embodiment of the first through fourth aspects of the invention using a removable urease cartridge in order to replenish the urease within the sorbent cartridge. The urease cartridge 65 can be located behind optional door 72 on the dialysis cabinet 61. In any embodiment of the first through fourth aspects of the invention, the urease cartridge 65 can be considered to be optionally removable. The particular location of the urease cartridge 65 is flexible. However, the urease cartridge 65 can be placed near inlet line 63 in certain configurations. The urease cartridge 65 can be fluidly connected to the sorbent cartridge 62 through inlet line 63. Outlet line 64 can connect the sorbent cartridge 62 to the rest of the dialysis flow path. The user can insert a urease cartridge 65 between cartridge inlet 66 and cartridge outlet 67. Water from water reservoir 68 can be directed into the urease cartridge 65 through cartridge inlet 66, dissolving the urease. The dissolved urease can then flow through cartridge outlet 67 and into sorbent cartridge 62 by inlet line 63 where the urease can be immobilized by alumina or silica within the sorbent cartridge 62. In any embodiment of the first through fourth aspects of the invention, dialysate or priming solution can be directed through the urease cartridge 65 in order to dissolve the urease. Water source 69 can be used to fill the water reservoir 68 and provide water for the dialysis session. Alternatively, in any embodiment of the first through fourth aspects of the invention, the water source can contain optionally a buffer and/or an additional excipient. The addition of urease can be controlled through user interface 70, with the user inputting necessary information with inputs 71.

Whenever the functional capacity of the urease in the sorbent cartridge 62 is reduced, the user can attach a new urease cartridge 65 to cartridge inlet 66 and cartridge outlet 67. The user can then direct the system to dissolve the urease within the urease cartridge 65 and to direct the resulting urease solution into the sorbent cartridge 62. After use, the user can remove the urease cartridge 65, or add a new urease cartridge to the system. Any mode of attachment of the urease cartridge 65 to the cartridge inlet 66 and cartridge outlet 67 is contemplated by the invention. In any embodiment of the first through fourth aspects of the invention, the urease cartridge 65 can attach by a screw-type attachment. The cartridge inlet 66 and cartridge outlet 67 can have threaded portions on the ends, comprising the male portion of a screw attachment. The urease cartridge 65 can have the female portion of the screw attachment disposed on either end. In order to remove or replace the urease cartridge 65, the user can screw or unscrew the urease cartridge 65 from the cartridge inlet 66 and cartridge outlet 67. Any other method of connecting the urease cartridge 65 to the cartridge inlet 66 and cartridge outlet 67 can be used.

Figure 5:
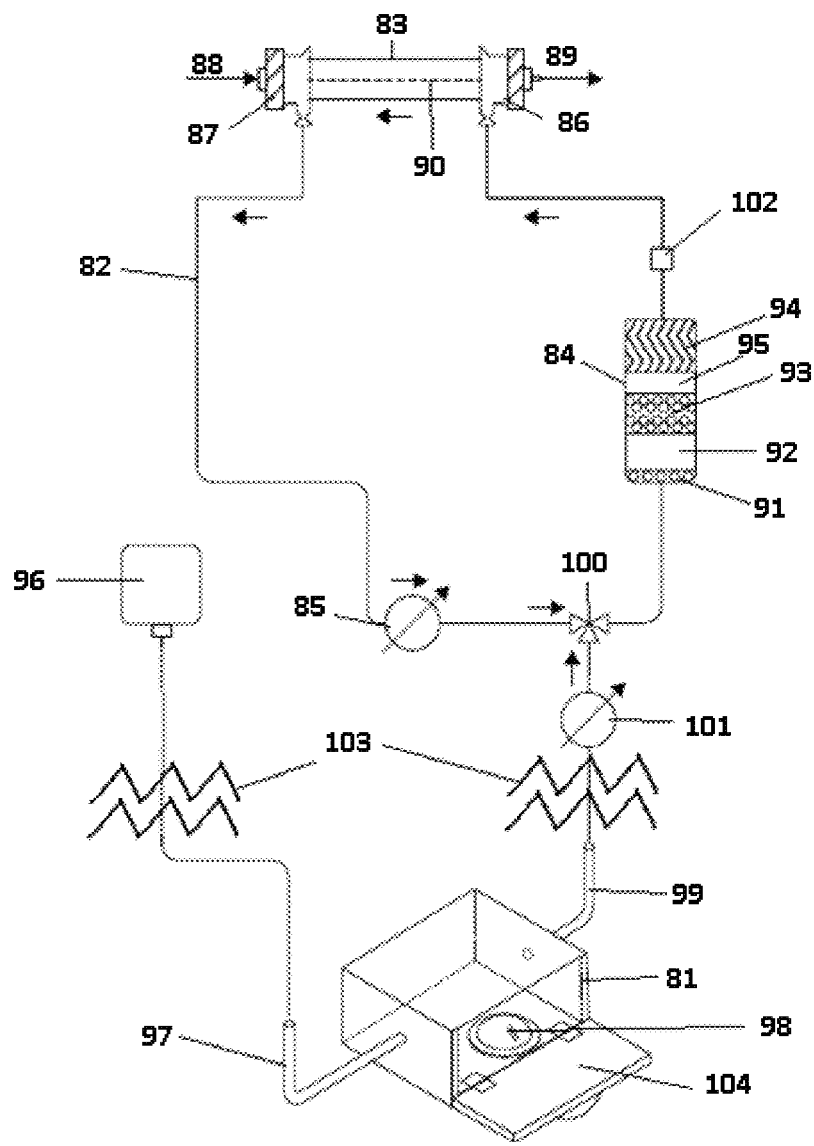
FIG. 5 is a combined schematic/representative drawing of a dialysis flow path including a sorbent cartridge and a urease compartment for addition of urease to the sorbent cartridge.

FIG. 5 shows a dialysis flow loop in accordance with one embodiment of the first through fourth aspects of the invention. The urease compartment 81 is shown as a schematic, but the dialysis flow loop 82 above lines 103 is shown as a representative drawing in FIG. 5. The dialysis flow loop 82 allows for the conveyance of fluid from the dialyzer 83 to the sorbent cartridge 84, and back to the dialyzer 83. Fluid in the dialysis flow loop 82 is moved through the dialysis flow loop 82 by dialysate pump 85. Blood is moved in an extracorporeal pathway (not shown) from the patient to the dialyzer 83 and back to the patient. Dialysate enters the dialyzer 83 through dialyzer inlet 86 and exits through dialyzer outlet 87. The patient's blood enters the dialyzer in the opposite direction, as shown by arrow 88, and exits as shown by arrow 89. In the dialyzer 83, solutes present in the blood of the patient travel across a semi-permeable membrane 90 and into the dialysis flow loop 82. The toxins are removed from the dialysate, or broken down into non-toxic components, in the sorbent cartridge 84. The sorbent cartridge 84 can contain urease adsorbed onto alumina or silica, and combinations thereof, as described herein.

The sorbent cartridge 84 can contain layers of sorbent materials as shown in FIG. 4. The sorbent cartridge can contain, in any embodiment of the first through fourth aspects of the invention, a layer of activated carbon 91, a layer of alumina or silica, and urease 92, a layer of zirconium oxide 93 and a layer of zirconium phosphate 94. One skilled in the art will understand that the sorbent materials within the sorbent cartridge 84 can be intermixed in any embodiment of the first through fourth aspects of the invention, as opposed to being arranged in layers. One skilled in the art will also understand that the precise order of the sorbent materials within the sorbent cartridge is flexible to a wide range of configurations, so long as the zirconium phosphate layer 94 is located downstream of the alumina or silica, and urease layer 92. For example, the first layer can be activated carbon, the second layer can contain zirconium oxide, the third layer can contain alumina or silica, and urease and the fourth layer can contain zirconium phosphate. Any order of layers with the zirconium phosphate layer downstream of the alumina or silica and urease layer is contemplated by this invention. In any embodiment of the first through fourth aspects of the invention, a second layer of alumina or silica 95 may be included without bound urease to prevent urease migration. In any embodiment of the first through fourth aspects of the invention, the sorbent materials may be separated into modules that are fluidly connected. In any embodiment of the first through fourth aspects of the invention, not all of the sorbent materials shown in FIG. 5 need to be included, and additional sorbent materials, such as ion exchange resins can be included in the sorbent cartridge 84. The urease in the sorbent cartridge 84 can break down urea present in the dialysate into carbon dioxide and ammonia, which can then be removed by zirconium phosphate or any other cation exchange resin.

In any embodiment of the first through fourth aspects of the invention, a layer of alumina or silica can be placed upstream of the layer of activated carbon. This ensures that portions of the urease injected into the sorbent cartridge are not removed from solution by the activated carbon prior to reaching the alumina or silica layer. In any embodiment of the first through fourth aspects of the invention, the alumina or silica layer can be downstream of the layer of activated carbon. There is not a requirement that urease binds with alumina or silica in order to function properly. Urease can function in order to breakdown urea into ammonium and carbon dioxide, without the urease being bound to the alumina or silica. Importantly, because urease is water soluble, the urease should bind to some hydrophobic material within the cartridge so that the urease doesn't simply dissolve and pass through the cartridge. Alumina or silica is generally used for this purpose, but any hydrophobic, non-water-soluble material could work for this purpose. In some cases, the urease can bind to the other sorbent materials within the cartridge, such as activated carbon, zirconium phosphate or zirconium oxide, without a reduction in urease activity. In any embodiment of the first through fourth aspects of the invention, the other sorbent materials, such as activated carbon, zirconium oxide or zirconium phosphate, can bind urease that migrates from the alumina or silica layer while the urease can remain active. In embodiments of the first through fourth aspects of the invention wherein the activated carbon layer is downstream of the alumina or silica layer, the activated carbon can act as a safety backup, to capture urease that migrates through the alumina or silica and would otherwise leave the sorbent cartridge. In any embodiment of the first through fourth aspects of the invention, a carbon loaded filter pad with a pore size large enough to allow urease to pass through the filter can be placed upstream of the alumina or silica layer. The carbon loaded filter pad can help to distribute the fluid flow through the cartridge, and remove trace contaminants in the starting water that could degrade the functionality of the urease. In any embodiment of the first through fourth aspects of the invention, the carbon loaded filter pad can have a pore size small enough to capture the urease.

The urease compartment 81 of the present invention can be positioned so that the urease compartment 81 is fluidly connected to the dialysis flow loop 82 as shown in FIG. 5. The urease compartment 81 should connect to the dialysis flow loop 82 upstream of the sorbent cartridge 84. Once the cover 104 of the urease compartment 81 has been closed, water from water reservoir 96 can be added to the urease compartment 81 through inlet line 97. The urease present in the urease compartment 81 can be in the form of solid urease in powder or block form, or a urease pouch 98. The fluid can dissolve the urease within the urease pouch 98. The dissolved urease can then travel to the dialysis flow path 82 by outlet line 99. In any embodiment of the first through fourth aspects of the invention, the addition of fluid to the dialysis flow loop 82 can be controlled by valve 100. Valve 100 can be any type of valve known in the art, including 2-way, 3-way, 4-way or any other type of valve. Urease pump 101 can provide the force necessary to move fluid from the urease compartment 81 to the dialysis flow loop 82. The fluid, containing dissolved urease, can travel to the sorbent cartridge 84 where the dissolved urease can be adsorbed onto the alumina or silica, and combinations thereof.

In any embodiment of the first through fourth aspects of the invention, optional urea detector 102 can be placed in the dialysis flow loop. The urea detector 102 can determine the amount of urea that has been converted to ammonia and carbon dioxide in the sorbent cartridge 84, as explained herein. If the amount of urea converted to ammonia and carbon dioxide is less than expected, there may be insufficient urease within the sorbent cartridge 84. In any embodiment of the first through fourth aspects of the invention, an insufficient amount of urea being converted to carbon dioxide and ammonia may trigger an alert to the user to add more urease to the system. In any embodiment of the first through fourth aspects of the invention, the urea detector 102 may be positioned inside the sorbent cartridge 84.

Figure 6:
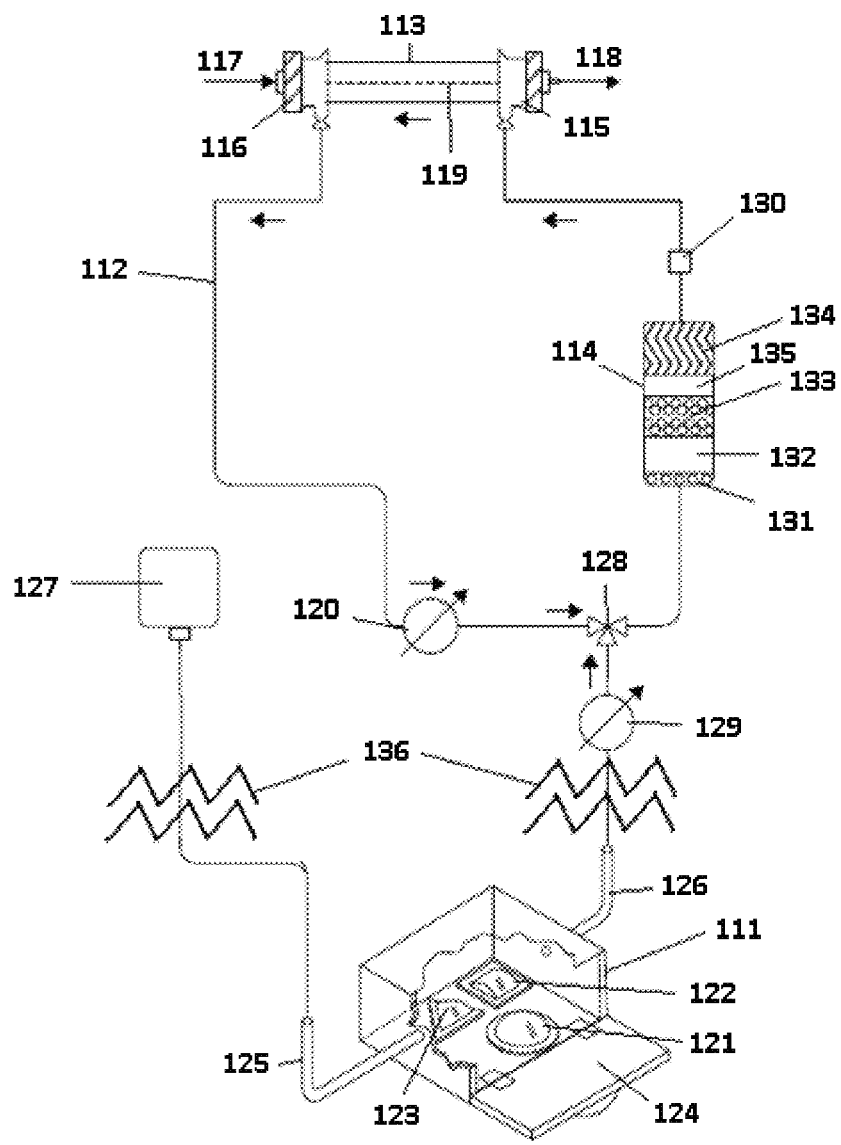
FIG. 6 is a combined schematic/representative drawing of a urease introduction system in a dialysis flow loop with the ability to use multiple urease pouches.

In any embodiment of the first through fourth aspects of the invention, the urease compartment can be adapted to receive multiple urease pouches, including pouches of different shapes or sizes as shown in FIG. 6. In FIG. 6, the urease compartment 111 is shown as a schematic, but the dialysis flow loop 112 above lines 136 is shown as a representative drawing in FIG. 6. The urease compartment 111 can be adapted to receive a circular urease pouch 121, a rectangular urease pouch 122, a triangular urease pouch 123, or combinations thereof. The urease pouches of the present invention can be in any shape, including a circular shape, a square shape, a triangular shape, a rectangular shape, a disc shape, a cylindrical shape, a spherical shape, a substantially rectangular shape, or a cubical shape. Any of the pouches can be of varying sizes. Adding multiple pouches, or differently sized pouches, adds to the adjustable aspect of the urease introduction system by allowing a greater range of urease to be added to the sorbent cartridge 114 than if only a single pouch is used. The urease compartment 111 of FIG. 6 can be fluidly connected to dialysis flow loop 112. The dialysis flow loop 112 conveys dialysate from the dialyzer 113 through dialyzer outlet 116 to the sorbent cartridge 114 and back to the dialyzer 113 through dialyzer inlet 115. Blood can travel through the dialyzer in the opposite direction, as shown by arrows 117 and 118 on the opposite side of semi-permeable membrane 119. Dialysate pump 120 provides the force necessary to circulate the dialysate. The sorbent cartridge 114 can contain, in any embodiment of the first through fourth aspects of the invention, a layer of activated carbon 131, a layer of alumina or silica and urease 312, a layer of zirconium oxide 133, a layer of zirconium phosphate 134, and optionally a second layer of alumina or silica 135. In any embodiment of the first through fourth aspects of the invention, the sorbent materials can be intermixed instead of in layers. In any embodiment of the first through fourth aspects of the invention, the order of the sorbent materials can be changed, so long as there is a zirconium phosphate layer downstream of an alumina or silica layer. In any embodiment of the first through fourth aspects of the invention, the alumina or silica layer can be upstream of the activated carbon layer.

The water reservoir 127 of FIG. 6 can be used to add water or any other aqueous solution (with or without a buffer or excipients) to the urease compartment 111 through inlet connector 125 after cover 124 is closed and sealed. The water can dissolve the urease within the sorbent pouches 121, 122, and 123 to create a urease solution. The urease solution can move out of the urease compartment 111 through outlet line 126 and into the dialysis flow loop 112. Valve 128 can control the movement of fluid from the urease compartment 111 to the dialysis flow loop 112. Urease pump 129 can provide the necessary force to move the urease solution. The urease solution can travel to the sorbent cartridge 114 where the urease can be immobilized by alumina or silica.

Optional urea detector 130 can be used to determine if there is sufficient urease within the sorbent cartridge 114. If there is insufficient urease in sorbent cartridge 114, the user can direct the addition of more urease as explained herein. In any embodiment of the first through fourth aspects of the invention, the dialysis system can automatically control the urease addition.

Figure 7:
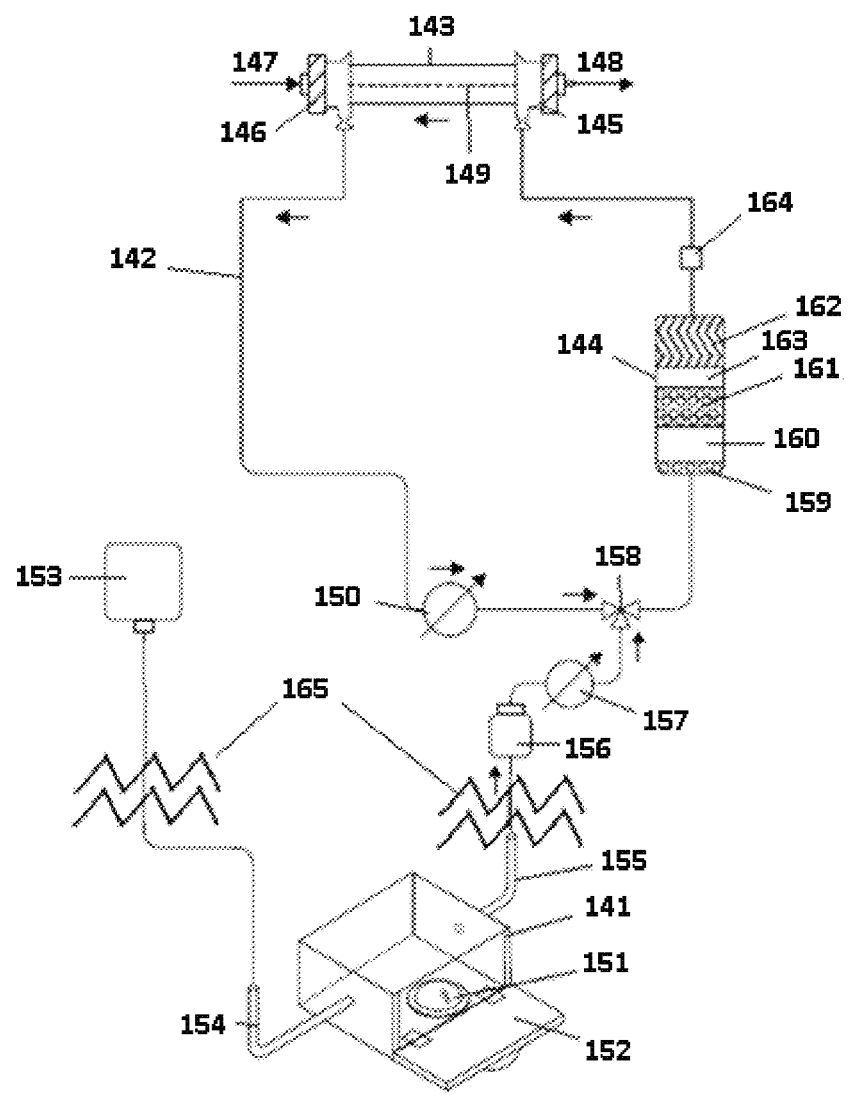
FIG. 7 is a combined schematic/representative drawing of a dialysis flow path including a sorbent cartridge and a urease compartment for addition of urease to the sorbent cartridge with a urease reservoir for holding urease.

An alternative embodiment of the first through fourth aspects of the invention dialysis is shown in FIG. 7. Urease compartment 141 is shown as a schematic, but the dialysis flow loop 142 above lines 165 is shown as a representative drawing in FIG. 7. Dialysate can be circulated through dialysis flow loop 142. The dialysate can travel through the flow loop from the dialyzer 143 to the sorbent cartridge 144, and back to the dialyzer 143. Dialysate pump 150 can provide the necessary force to drive the dialysate through the dialysis flow loop 142. Dialysate can enter the dialyzer 143 through inlet connector 145 and exit the dialyzer 143 through outlet connector 146. Blood from the patient can travel through the dialyzer 143 in the opposite direction, as shown by arrows 147 and 148. Impurities in the blood can move across semi-permeable membrane 149, enter the dialysate, and be removed by the sorbent cartridge 144. The sorbent cartridge 144 can contain, in any embodiment of the first through fourth aspects of the invention, a layer of activated carbon 159, a layer of alumina or silica and urease 160, a layer of zirconium oxide 161, a layer of zirconium phosphate 162, and optionally second alumina layer 163. In any embodiment of the first through fourth aspects of the invention, the sorbent materials can be intermixed instead of in layers, and can be placed in the sorbent cartridge in any order, so long as zirconium phosphate is present downstream of the alumina or silica. In any embodiment of the first through fourth aspects of the invention, the alumina or silica layer can be positioned upstream of the activated carbon layer.

The urease compartment 141 can be fluidly connected to the dialysis flow loop 142. The urease addition flow path can comprise a urease pump 157 and urease reservoir 156. In order to add urease to the sorbent cartridge 144, after closing of the door 152 to seal the urease compartment 141, water from water source 153 can be added to the urease compartment 141 through water line 154. The urease in the urease compartment 141, either in urease pouch 151 or in the form of solid urease can be dissolved by the water added to the urease compartment 141. The resulting solution can be pumped by urease pump 157 into urease reservoir 156 through outlet line 155. When the system requires additional urease to be added to the sorbent cartridge 144, urease pump 157 can pump the urease solution in reservoir 156 into the dialysis flow path 142, moving the dissolved urease into the sorbent cartridge 144 where the urease can be adsorbed onto alumina or silica, and combinations thereof, within the sorbent cartridge 144. Valve 158 can allow for control of the addition of urease into the dialysis flow path 142. In any embodiment of the first through fourth aspects of the invention, the dialysis system can automatically control valve 158 and pump 157 to add urease to the sorbent cartridge 144 when needed. In any embodiment of the first through fourth aspects of the invention, the user can direct the control of valve 158 and pump 157 to add urease to the sorbent cartridge 144.

In any embodiment of the first through fourth aspects of the invention, optional urea detector 164 can be included in the fluid flow path at a location downstream of the urease and alumina or silica layer 160 of the sorbent cartridge 144, as described herein.

In any embodiment of the first through fourth aspects of the invention, the urease reservoir 156 can be large enough to contain enough urease solution for several dialysis sessions. In any embodiment of the first through fourth aspects of the invention, the urease reservoir 156 can be large enough to contain a day's worth or more of urease. A larger amount of urease can be placed into urease compartment 141, dissolved, and directed into urease reservoir 156 as explained herein. The system can then meter out the specific amount of urease needed for a particular dialysis session. In any embodiment of the first through fourth aspects of the invention, computer systems and related control components such as pumps and actuators can automatically meter out a correct amount of urease based on the needs of the particular patient as explained herein. The system can direct the addition of urease into the dialysis flow loop 142 whenever necessary, such as before each dialysis session. A large urease reservoir 156 thus enables the user to add urease to the system periodically, but allows urease addition into the sorbent cartridge 144 whenever urease addition is necessary.

Preferably, the addition of urease to the sorbent cartridge in the flow loops shown in FIGS. 5-7 will occur during priming of the dialysis flow loop. Adding urease during priming of the dialysis flow loop can allow for loading the urease into the sorbent cartridge prior to dialysis, and eliminate the need for the dialysate to dissolve the urease during a dialysis session. This, in turn, eliminates the need to expose the urease compartment to the outside environment during a dialysis session. An amount of urease required may be reduced by introducing the urease only when urease introduction is needed such as after priming of the system in preparation for use. One of ordinary skill can provide a specific amount of urease needed for a particular patient via prescription thereby customizing the amount of urease required to the specific patient. The amount of urease added can be based on the patient (size, weight, BUN, etc.). Such patient customization or prescriptions can be performed in lieu of a sensor-based system or in conjunction with such sensor-based systems. In particular, the sensor-based systems having sensors capable of providing feedback regarding an amount of urease contained in the system and provides an input to further adjust the amount of urease required. Urease can be added to the sorbent cartridge at any point, including before, during, or after a dialysis session.

The urease compartments shown in FIGS. 5-7 are drawn larger than necessary in order to show details of the urease compartments. In any embodiment of the first through fourth aspects of the invention, the actual size of the urease compartment can be selected based on the expected amount of urease to be added by either solid urease or a urease pouch. For example, if most patients require 0.1 g of urease the urease compartment can have a size adapted for receiving either about 0.1 g of solid urease or a urease pouch containing about 0.1 g of solid urease. Further, the size and shape of the urease compartment is not limited to any particular shape or size and can be adapted to fit within tight spaces inside a dialysis system.

Figure 8:
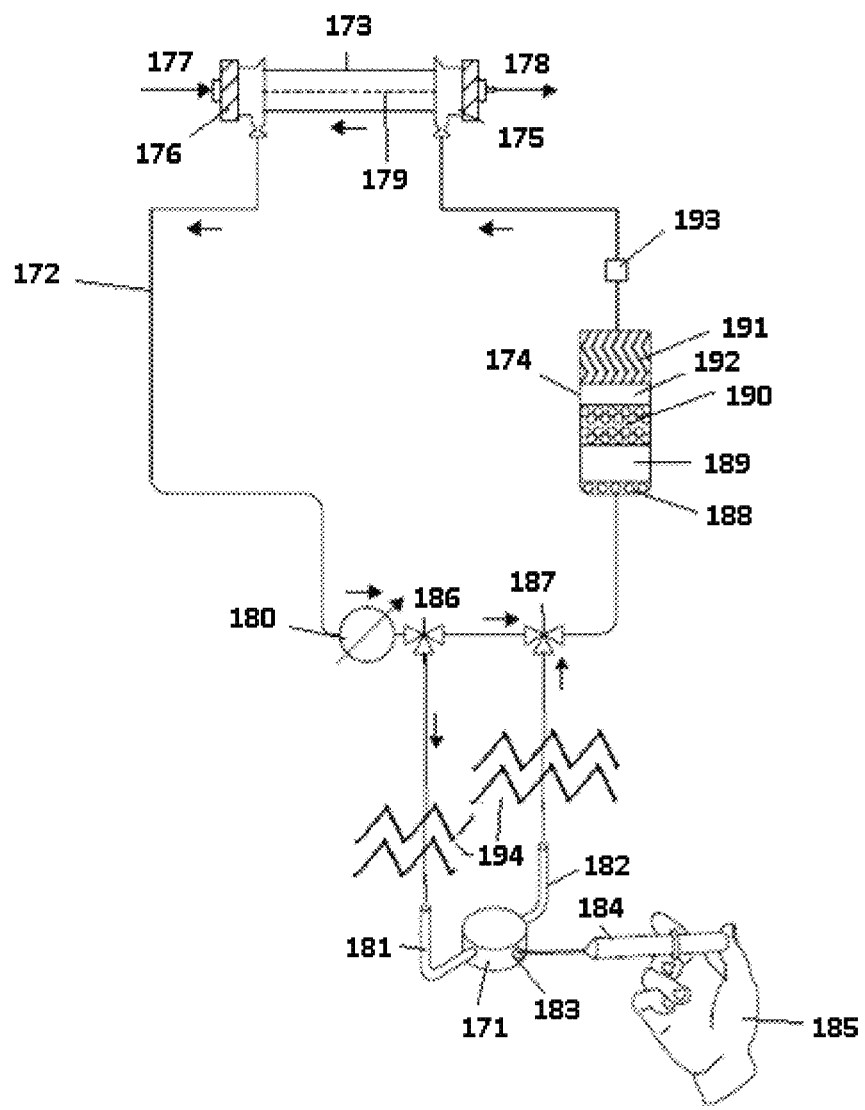
FIG. 8 a combined schematic/representative drawing of a dialysis flow path including a sorbent cartridge and a urease injection system for addition of urease to the sorbent cartridge.

FIG. 8 shows a dialysis flow loop with an injection site for urease addition. The urease injection system is shown as a schematic, but that the dialysis flow loop 172 above lines 194 is shown as a representative drawing in FIG. 8. Similar to FIG. 5, the dialysis flow loop 172 allows for the circulation of dialysate between the dialyzer 173 and the sorbent cartridge 174, with dialysate pump 180 providing the force necessary to circulate the dialysate. The dialysate can enter dialyzer 173 through dialyzer inlet 175 and exit through dialyzer outlet 176. Blood can travel through the dialyzer 173 in the opposite direction as shown by arrows 177 and 178 on the opposite side of semi-permeable membrane 179 as the dialysate. The sorbent cartridge 174 can contain, in any embodiment of the first through fourth aspects of the invention, a layer of activated carbon 188, a layer of alumina or silica and urease 189, a layer of zirconium oxide 190, a layer of zirconium phosphate 191, and optionally a second alumina or silica layer 192. In any embodiment of the first through fourth aspects of the invention, the sorbent materials can be intermixed instead of in layers, or be present in the sorbent cartridge 174 in any order so long as the zirconium phosphate layer is downstream of the alumina or silica. In any embodiment of the first through fourth aspects of the invention, a layer of alumina or silica can be downstream of the layer of activated carbon.

A user 185 can add a urease solution through injection port 171 in FIG. 8 by syringe 184 or any other method of adding a urease solution into the injection port 171. The urease solution, once injected, can travel through outlet line 182 into the dialysis flow path 172 and can travel to the sorbent cartridge 174 and become adsorbed by alumina or silica within the sorbent cartridge 174.

The injection port 171 can be sealed with a pierceable septum 183 in any embodiment of the first through fourth aspects of the invention, as described herein. By injecting the urease using a syringe 184 through a septum 183, the urease does not need to be exposed to the outside environment. This allows for an injection of urease into the sorbent cartridge 174 during a dialysis session, without the risk of introducing potentially hazardous environmental toxins. Injection port 171 can be in a parallel flow loop to the dialysis flow loop 172. This allows for direct addition of urease into the dialysis flow loop 172 and the sorbent cartridge 174. In any embodiment of the first through fourth aspects of the invention, valves 186 and 187 can be used to control the flow of fluid through the urease injection flow loop. In any embodiment of the first through fourth aspects of the invention, valve 186 can be open to the dialysis flow loop 172 and the urease injection flow loop so that fluid from the dialysis flow loop 172 flows into the injection port 171 through inlet line 181, and out through outlet line 182, flushing all of the urease into the dialysis flow loop 172. In any embodiment of the first through fourth aspects of the invention, water from a water reservoir (not shown) that is fluidly connected to injection port 171 can be used to flush out the injection port 171. Valve 187 can be used to control the addition of urease from the urease injection port 171 into the dialysis flow loop 172. Critically, the adjustability of the amount of urease to be added in-session can provide flexibility in type of treatment delivered and therapy goals. The adjustable amount of urease can further provide for personalization of treatment and also result in a system that can be easily adapted to provide treatment for different patients. Adjustability in urease can reduce waste and tailor treatment to specific goals not possible with systems having not mechanism for adjusting an amount of urease being used during dialysis or across different treatment sessions.

In any embodiment of the first through fourth aspects of the invention, optional urea detector 193 can be included in the fluid flow path at a location downstream of the urease and alumina or silica layer 189 of the sorbent cartridge 174, as described herein.

Figure 9:
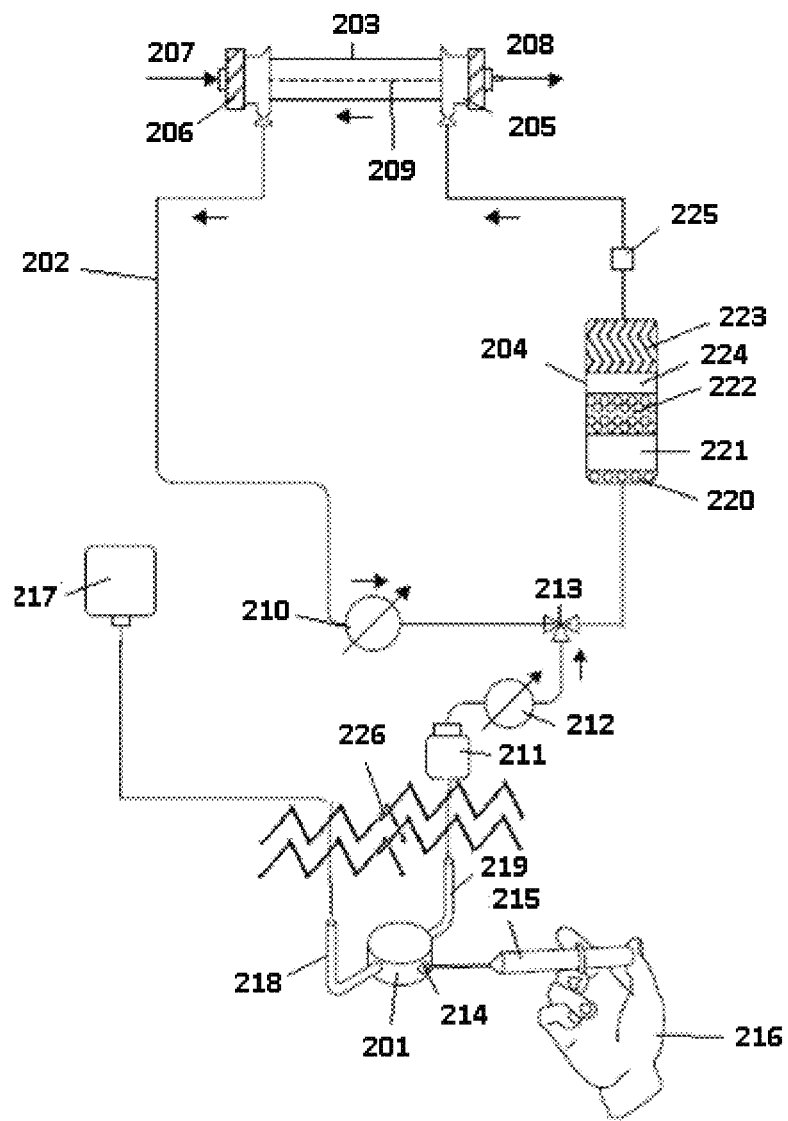
FIG. 9 is a combined schematic/representative drawing of a dialysis flow path including a sorbent cartridge and a urease compartment for addition of urease to the sorbent cartridge with a urease reservoir for holding the injected urease.

In an embodiment of the first through fourth aspects of the invention, shown in FIG. 9, the urease injection port 201 can be fluidly connectable to a urease reservoir 211. The urease injection portion is shown as a schematic, but dialysis flow loop 202 above lines 226 is shown as a representative drawing in FIG. 9. Dialysate in the flow loop can be circulated between dialyzer 203 and sorbent cartridge 204. The dialysate can enter the dialyzer 203 through inlet 205 and exit through outlet 206. Dialysate pump 210 can provide the force necessary for circulation of the dialysate. Blood from a patient can be circulated on the opposite side of the semi-permeable membrane 209 of the dialyzer 203 in the opposite direction, as shown by arrows 207 and 208.

The urease reservoir 211 can be fluidly connectable to dialysis flow path 202 by outlet 219, connecting upstream of the sorbent cartridge 204. The user 216 can inject a fresh amount of urease into the urease injection port 201 with syringe 215 through septum 214, and into the urease reservoir 211. As needed, pump 212 can move the urease solution in the urease reservoir 211 into the dialysis flow path 202. The urease can be adsorbed onto the alumina or silica in the sorbent cartridge 204 for use in dialysis. Valve 213 can control the addition of urease to the dialysis flow path 202 and into the sorbent cartridge 204. In any embodiment of the first through fourth aspects of the invention, valve 213 and pump 212 can be controlled automatically by the dialysis system whenever urease addition is necessary. In any embodiment of the first through fourth aspects of the invention, the user can control valve 213 and pump 212 to add the urease when necessary.

In any embodiment of the first through fourth aspects of the invention, water from water reservoir 217 can be passed through the urease injection port 201 in order to flush out all the urease from the injection port 201. The water can enter the injection port through inlet 218, and flush the urease through outlet 219 into the urease reservoir 211.

In any embodiment of the first through fourth aspects of the invention, the urease reservoir 211 can be large enough to contain enough urease solution for several dialysis sessions. The urease reservoir 211 can thus act as a bulk supply of urease. A larger amount of urease can be injected into urease injection port 201, and directed into urease reservoir 211 as explained herein. The system can then meter in the urease into the dialysis flow loop 202 whenever urease addition is necessary, enabling the user to only inject the urease solution occasionally, but allowing the system to add urease to the sorbent cartridge 204 as required.

In any embodiment of the first through fourth aspects of the invention, a syringe type mechanism can be used to meter in urease from the bulk supply. An automated syringe (not shown), similar to a heparin pump, can be used to move urease from the bulk supply in the urease reservoir 211 to the sorbent cartridge 204. The amount of urease metered into the sorbent cartridge 204 from the urease reservoir 211 can be based on the specific needs of the patient, as described herein.

The sorbent cartridge 204 can contain, in any embodiment of the first through fourth aspects of the invention, a layer of activated carbon 220, a layer of alumina or silica, and urease 221, a layer of zirconium oxide 222, a layer of zirconium phosphate 223 and optionally a second layer of alumina or silica 224. In any embodiment of the first through fourth aspects of the invention, the sorbent materials can be intermixed instead of in layers, or be present in any order so long as zirconium phosphate is downstream of an alumina or silica layer. In any embodiment of the first through fourth aspects of the invention, a layer of alumina or silica can be positioned upstream of the layer of activated carbon.

In any embodiment of the first through fourth aspects of the invention, urea detector 225 can be placed downstream of the sorbent cartridge 204. A urea detector 225 can detect urea that has not been converted to $CO_2$ and ammonia by urease. If urea is present in the dialysate, there may be insufficient urease in the sorbent cartridge. If urease is detected in the dialysate after the dialysate passes through the sorbent cartridge, fresh urease can be added to the sorbent cartridge from urease reservoir 211 by action of urease pump 212 and the opening of valve 213. In any embodiment of the first through fourth aspects of the invention, the system may give the user an audio or visual alert if the urea detector detects urea in the spent dialysate after passing through the urease containing module. In any embodiment of the first through fourth aspects of the invention, alumina, silica, or ZP can provided via the of the urease injection port 201 where flow can be routed via inlet 218 and outlet 219. The alumina, silica, or ZP can be provided in any form. In order to prevent binding with urease that can also be added via the urease injection port 201. The addition of alumina and silica can be provided in sequence, or separately, to avoid binding to urease.

Figure 10:
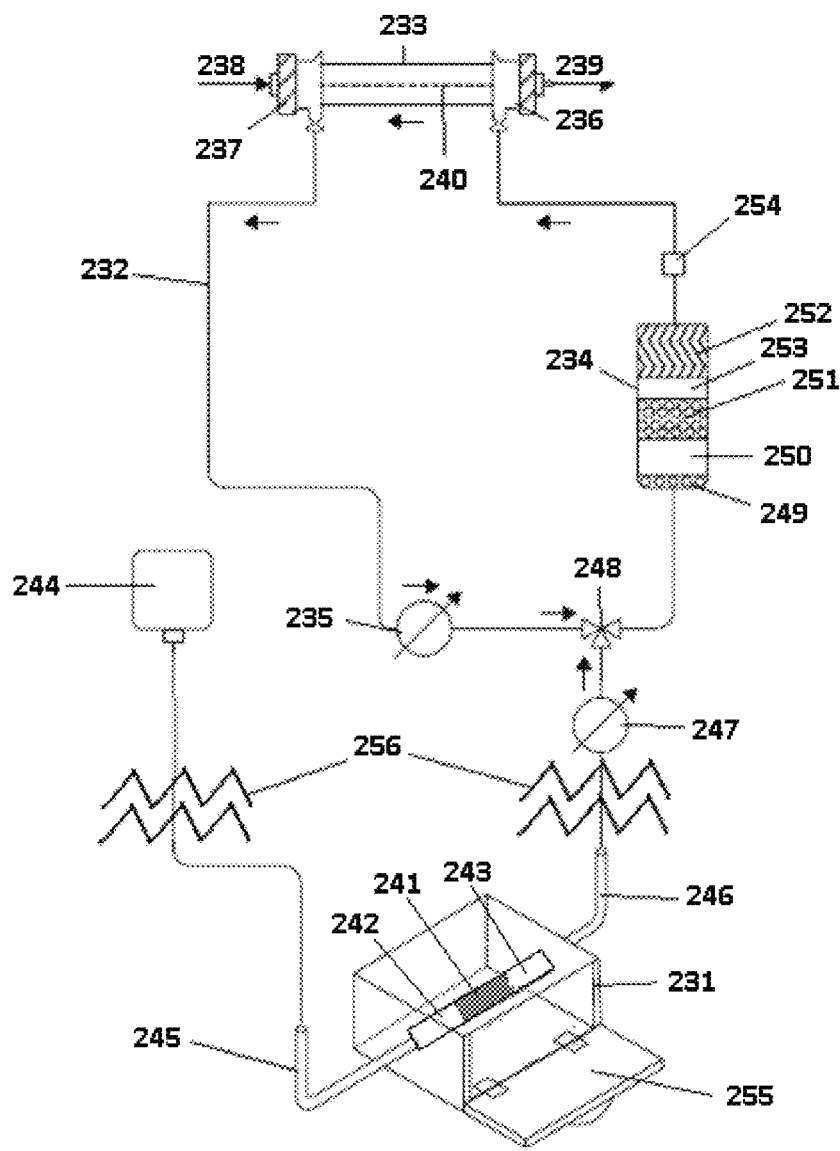
FIG. 10 is a combined schematic/representative drawing of a dialysis flow path including a sorbent cartridge and a removable urease cartridge for addition of urease to the sorbent cartridge.

FIG. 10 shows a dialysis flow loop using a removable urease cartridge as the method to replenish urease. Urease compartment 231 is shown as a schematic, but dialysis flow loop 232 above lines 256 is shown as a representative drawing in FIG. 10. Dialysate can be circulated through dialysis flow loop 232. The dialysate can travel through the flow loop from the dialyzer 233 to the sorbent cartridge 234, and back to the dialyzer 233. Dialysate pump 235 can provide the necessary force to drive the dialysate through the dialysis flow loop 232. Dialysate can enter the dialyzer 233 through inlet connector 236 and exit the dialyzer 233 through outlet connector 237. Blood from the patient can travel through the dialyzer 233 in the opposite direction, as shown by arrows 238 and 239. Impurities in the blood can move across semi-permeable membrane 240, enter the dialysate, and be removed by the sorbent cartridge 234. The sorbent cartridge 234 can contain, in any embodiment of the first through fourth aspects of the invention, a layer of activated carbon 249, a layer of alumina or silica and urease 250, a layer of zirconium oxide 251, a layer of zirconium phosphate 252, and optionally second alumina layer 253. In any embodiment of the first through fourth aspects of the invention, the sorbent materials can be intermixed instead of in layers, and can be placed in the sorbent cartridge in any order, so long as zirconium phosphate is present downstream of the alumina or silica.

The removable urease cartridge 241 can be fluidly connected to the dialysis flow loop 232. In any embodiment of the first through fourth aspects of the invention, the removable urease cartridge 241 can be located within compartment 231 behind door 255 in order to protect the cartridge 241 and connections. The urease addition flow path can comprise a urease pump 247 and water reservoir 244. In order to add urease to the sorbent cartridge 234, water from water source 244 can be directed through the urease cartridge 241 through water line 245. The urease in the urease cartridge 241 can be dissolved by the water, buffer or other aqueous solution added from water source 244. The resulting solution can be pumped by urease pump 247 through outlet line 246. Urease pump 247 can pump the urease solution into the dialysis flow path 232, moving the dissolved urease into the sorbent cartridge 234 where the urease can be adsorbed onto alumina or silica within the sorbent cartridge 234. Valve 248 can allow for control of the addition of urease into the dialysis flow path 232. In any embodiment of the first through fourth aspects of the invention, the dialysis system can automatically control valve 248 and pump 247 to add urease to the sorbent cartridge 234 when needed. In any embodiment of the first through fourth aspects of the invention, the user can direct the control of valve 248 and pump 247 to add urease to the sorbent cartridge 234.

In any embodiment of the first through fourth aspects of the invention, optional urea detector 254 can be included in the fluid flow path at a location downstream of the urease and alumina or silica layer 250 of the sorbent cartridge 234, as described herein.

The removable urease cartridge 241 can be connected to the urease flow path through inlet connector 242 and outlet connector 243. As explained herein, the connections can be any type of connection known in the art, including screw type connections, snap on connections, or any other type. In any embodiment of the first through fourth aspects of the invention, the removable urease cartridge 241 can comprise filters in order to remove any particulate matter before water, buffer or other aqueous solution enters or leaves the urease cartridge 241. After use, the user can disconnect and remove the removable urease cartridge 241 from the system, and replace the used cartridge 241 with a fresh urease cartridge.

Figure 11:
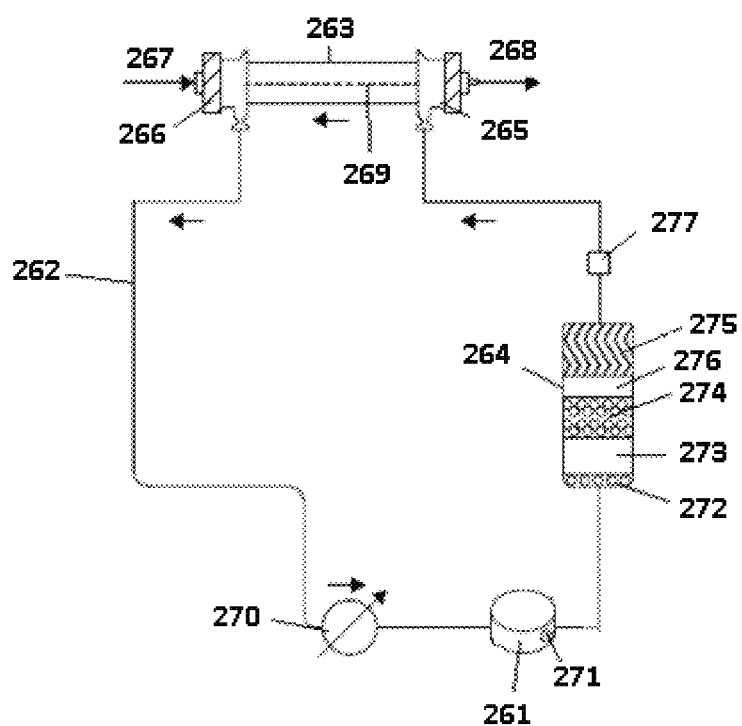
FIG. 11 is a representative drawing of a dialysis flow path with an inline urease injection port.

In any embodiment of the first through fourth aspects of the invention using any type of urease introduction means described herein, the urease introduction can be in line with the sorbent cartridge. FIG. 11 shows an in-line system using a urease injection port. The urease injection port 261 can be located in the dialysis flow loop 262. The dialysate can travel through the flow loop 262 from the dialyzer 263 to the sorbent cartridge 264, and back to the dialyzer 263. Dialysate pump 270 can provide the necessary force to drive the dialysate through the dialysis flow loop 262. Dialysate can enter the dialyzer 263 through inlet connector 265 and exit the dialyzer 263 through outlet connector 266. Blood from the patient can travel through the dialyzer 263 in the opposite direction, as shown by arrows 267 and 268. Impurities in the blood can move across semi-permeable membrane 269, enter the dialysate, and be removed by the sorbent cartridge 264. The sorbent cartridge 264 can contain, in any embodiment of the first through fourth aspects of the invention, a layer of activated carbon 272, a layer of alumina or silica and urease 273, a layer of zirconium oxide 274, a layer of zirconium phosphate 275, and optionally second alumina layer 276. In any embodiment of the first through fourth aspects of the invention, the sorbent materials can be intermixed instead of in layers, and can be placed in the sorbent cartridge in any order, so long as zirconium phosphate is present downstream of the alumina or silica.

In any embodiment of the first through fourth aspects of the invention, optional urea detector 277 can be included in the fluid flow path 262 at a location downstream of the urease and alumina or silica layer 273 of the sorbent cartridge 264, as described herein.

Whenever addition of fresh urease to the system becomes necessary, the user can inject a urease solution into the urease injection port 261 through pierceable septum 271. The urease solution in any embodiment of the first through fourth aspects of the invention, can directly enter the dialysis flow loop 262, and travel to the sorbent cartridge 264 where the urease can be immobilized by alumina or silica.

In any embodiment of the first through fourth aspects of the invention, the urea detector shown in each of the figures can be placed in the dialysis flow path downstream of the sorbent cartridge. In any embodiment of the first through fourth aspects of the invention, the urea detector can be placed in the sorbent cartridge at any point after the alumina or silica in the sorbent cartridge.

Without being limited to any particular method, there are two general methods for the measurement of urea nitrogen. The diacetyl, or Fearon, reaction develops a yellow chromogen with urea, and this is quantified by photometry. The Fearon reaction has been modified for use in autoanalyzers and generally gives relatively accurate results. In the more specific enzymatic methods, the enzyme urease converts urea to ammonia and carbonic acid. These products, which are proportional to the concentration of urea in the sample, are assayed in a variety of systems, some of which are automated. One system checks the decrease in absorbance at 340 mm when the ammonia reacts with alpha-ketoglutaric acid. The Astra system measures the rate of increase in conductivity of the solution in which urea is hydrolyzed. The specimen should not be collected in tubes containing sodium fluoride because the fluoride inhibits urease. Also chloral hydrate and guanethidine have been observed to increase BUN values. Alternatively, urea can be measured indirectly by an ammonia detector located downstream of the urease layer and upstream of the zirconium phosphate layer. In general, low or no ammonia detected in fluid after passing through the urease layer but before reaching the zirconium phosphate layer may indicate that there is insufficient urease during a session, under the assumption that urea is being removed by the dialyzer.

In any embodiment of the first through fourth aspects of the invention, a urea detector can detect ammonia in the system that can indicate that zirconium phosphate contained within the system has reached capacity. In any embodiment of the first through fourth aspects of the invention, the amount of ammonia produced can be a function of the zirconium phosphate capacity and the system can determine if zirconium phosphate is required by the system.

Any method of detecting the amount of urea that is converted to ammonia in the sorbent cartridge is within the scope of the first through fourth aspects of the invention. In addition to the methods above, the detection can be accomplished by any means known in the art, including but not limited to, the use of an optical sensor, a chemical sensor, a blood urea nitrogen assay, an ammonium sensor, or any combination thereof.

The amount of urea converted to ammonia by the urease in a sorbent cartridge can be detected, such as by detecting the amount of ammonia or urea in the dialysate before and after passage through the sorbent cartridge. Not enough urea being converted to ammonia, as shown by urea in the fluid after the sorbent cartridge or a lack of ammonia in the fluid after the sorbent cartridge, is indicative of a lack of urease in the sorbent cartridge and fresh urease can be added.

Before each dialysis session, after priming of the dialysis system, after a set number of dialysis sessions, whenever the amount of the urease within the module is reduced, or after each time the rest of the sorbent materials are recharged, the user would only need to inject the contents of the sorbent container into the urease injection port. In any embodiment of the first through fourth aspects of the invention, the system can prompt the user to inject a fresh urease solution into the sorbent cartridge before each dialysis session, after priming of the dialysis system, after a set number of dialysis sessions, or after the other sorbent materials have been recharged. In any embodiment of the first through fourth aspects of the invention, the urease solution injected into the urease injection port can be of a higher concentration. The urease injected can then be diluted by water as the water flows in the fluid flow path into the sorbent cartridge.

Figure 12:
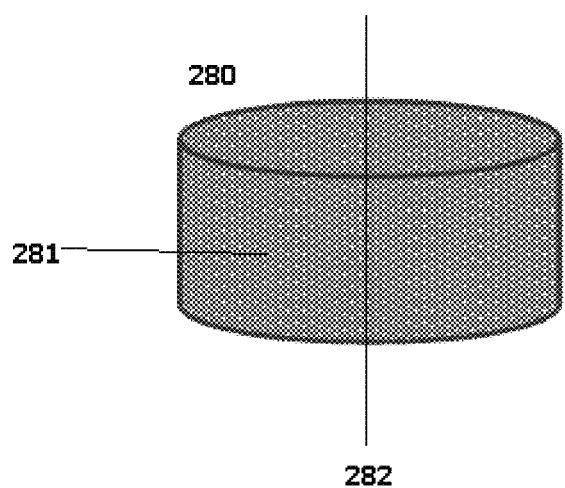
FIG. 12 shows a perspective view of a urease pouch for use in the system.

One embodiment of a urease pouch that can be used in the first through fourth aspects of the invention is shown in FIG. 12. Urease pouch 280 can contain urease 281. In any embodiment of the first through fourth aspects of the invention, the urease pouch can contain solid urease or powdered urease. The urease pouch 280 can have pores with a size small enough so that urease cannot pass through the urease pouch in its solid or undissolved form, but that are large enough to allow water to pass into and out of the urease pouch 280. The optimal pore size of the urease pouch 280 can be determined by the particle size of the urease. Hence, one of ordinary skill in the art can determine the proper pore size to use for the urease pouch 280 for a given batch of urease. When dissolved in water, the urease solution can pass through the pores of the urease pouch 280. In this way the user can place the urease pouch 280 inside the urease compartment as explained above. The system can then direct fluid into the urease compartment, which can enter the urease pouch 280 and dissolve the urease. The resulting urease solution then travels to the sorbent cartridge, where the urease is adsorbed by alumina or silica, and combinations thereof. The porous material of the urease pouch 280 can include, but is not limited to, bolting cloth, cotton, ashless filter paper, Dacron, polyethylene terephthalate, or metal.

As described, the urease pouches of the first through fourth aspects of the invention can be in any shape, including a circular shape, a square shape, a triangular shape, a rectangular shape, a disc shape, a cylindrical shape, a spherical shape, a substantially rectangular shape, or a cubical shape. Each shape described can be substantially in the form described and can vary in dimensions without departing from the invention. For example, a pouch having a generally spherical shape, which is slightly ovoidal is contemplated by the invention. Similarly, a disc having a tapered end on one or more ends to form a cone or being conoidal in form is also contemplated. Such variations from the generally described geometrical shapes are each encompassed by the invention. In any embodiment of the first through fourth aspects of the invention, the upwardly extending walls of the urease pouch 280 can slope inward toward axis 282, creating a urease pouch with a top surface having a smaller surface area than the bottom surface. In any embodiment of the first through fourth aspects of the invention, the upwardly extending walls can slope away from axis 282, creating a urease pouch with a top surface having a larger surface area than the bottom surface. In any embodiment of the first through fourth aspects of the invention, the upwardly extending walls can be parallel to axis 282, creating a urease pouch with a top and bottom surface area that are equal. In any embodiment of the first through fourth aspects of the invention, the size and shape of urease pouch 280 can be selected based on the size and shape of the interior portion of the urease compartment.

In any embodiment of the first through fourth aspects of the invention, the urease pouch can be made out of a material that is water soluble. Non-limiting examples include polyvinyl alcohols, thermoplastic fibers, or any other water soluble material capable of containing urease. When a water soluble material is used for the urease pouch, the user need only place the urease pouch in the urease compartment. The system will direct water into the urease compartment, where the urease pouch will be dissolved. The water will also dissolve the urease, and move the dissolved urease into the sorbent cartridge where the urease will be adsorbed by alumina or silica, and combinations thereof.

The first through fourth aspects of the invention relate to loading urease into a sorbent cartridge in solution form, as opposed to loading a dry powder of urease into a sorbent column. In order to test the effectiveness of urease solution injection for loading urease into a sorbent cartridge, as opposed to loading urease to a column as a dry powder, several experiments were run. These experiments are described herein as Examples 1-4. Example 1 refers to the loading of urease onto a column using a dry powder loading procedure. Examples 2 and 3 are the analysis of the urease migration and urea conversion obtained from the dry powder loading procedure of Example 1. Example 4 relates to the loading and analysis of urease onto a column using a urease solution.

Example 1

An Ace Glass 25 millimeter Adjusta-Chrom Jacketed Column (P/N 5819) was packed with a mixture of 3.001 grams activated alumina (Shandong Luye Co, Lot 20140811-1) and 0.0040 grams of purified urease (Tokyo Chemical Industry, Lot P7DWG-TJ). An additional 9.0070 grams of activated alumina (Shandong Luye Co, Lot 20140811-1) was added to the column and the outlet frit and plunger were adjusted so that no dead space existed above the alumina layer and locked into place. Heated water was circulated through the external jacket of the column to maintain a temperature of 37° C. throughout the experiment. The column was primed by pumping base buffer (115 mMol sodium chloride and 25 mMol sodium bicarbonate) at 15 ml/minute until the liquid level reached the top of the alumina then held for five minute without flow to allow the urease to distribute and bind to the alumina. After the hold period the priming solution flow was restarted at 15 ml/min for an additional 5 minutes to complete the priming sequence. When the priming sequence was completed the column feed was changed to a test solution containing 25 mMol/Liter of urea (Sigma Aldrich) in base buffer. The flow rate was maintained at 15 mL/min for 60 minutes. The column effluent was collected for urease migration analysis and separate 8 mL samples were collected after 10, 30 and 60 minutes of test solution flow for urease conversion testing.

Example 2

A urea challenge solution was made containing 400 mMol/Liter phosphate buffer and 400 mMol/L urea. A 1.8 mL sample from the pooled column effluent from Example 1 was mixed with 1.8 mL of the urea challenge solution and incubated at room temperature for 10 minutes. Ammonium levels in the solution were measured using a Nova BioProfile 300 analyzer every 10 minutes over a period of 50 minutes. The ammonium concentration was plotted as a function of time and a linear regression was performed to determine the urease activity of the solution. The urease activity was then multiplied by the total volume of effluent run through the column to determine the total urease units (IU) that migrated during the test. For Example 1 the result was 53 International Units of migrated urease.

Example 3

The test samples collected at 10, 30 and 60 minutes in Example one were used for this analysis. A 0.8 mL aliquot of test sample was mixed with a 0.8 mL aliquot of 400 mM/L phosphate buffer and mixed vigorously. The ammonium concentration was determined using the Nova BioProfile 300 analyzer using the automated machine procedure. The results were compared to a standard curve measure in the same way using standard of known concentration. The ammonium concentration in the test sample is used to calculate the percent urea conversion for the urease/alumina reactor. For Example 1 the result was 53.4% urea conversion.

Example 4

The test system of Example 1 was modified to include a three way valve in the inlet feed line. The three way valve had one port compatible with a luer lock syringe and the other ports connected to the test solution and test column inlet. The Ace Glass 25 millimeter Adjusta-Chrom Jacketed Column was packed with 12.001 grams of alumina (Shandong Luye Co, Lot 20140811-1). A solution of 0.0079 grams urease (Tokyo Chemical Industry, Lot P7DWG-TJ) was mixed in 8.0 mL of base buffer (115 mMol sodium chloride and 25 mMol sodium bicarbonate) to make a solution of approximately 300 IU/mL. The urease was charged into the reactor by injecting 1.3 mL of base buffer, followed by 4.0 mL of urease solution and 1.8 mL of base buffer. The base buffer was used to fill the inlet line before introducing the urease and to ensure all the urease was flushed out of the inlet feed line and into the alumina. After introduction of the urease, the column was tested according to the method described in Examples 2-3. The urease migration for this test column was 47 International Units and the urea conversion was 67.4%.

The results of the experiments in Examples 1-4 are summarized in Table 1. As can be seen in Table 1, the results of the urease solution loading were comparable to the results obtained with dry powder loading. The results demonstrate that a liquid load is possible without all of the enzyme migrating out of the column.

TABLE 1

| Method of Urease Loading | Urease Migration | Urea Conversion |
| --- | --- | --- |
| Dry Powder Loading (Example 1) | 53 IU | 53.4% |
| Urease Solution Loading (Example 4) | 47 IU | 67.4% |

In any embodiment of the first through fourth aspects of the invention, other sorbent materials can be recharged by passing a fluid containing the correct solutes through the material. For example, zirconium phosphate can be recharged by passing a fluid containing hydrogen and sodium ions through the zirconium phosphate. The hydrogen and sodium ions will replace the ammonium, potassium, calcium, magnesium or other ions removed by the zirconium phosphate during dialysis, and thereby place the zirconium phosphate back in condition to be used in sorbent dialysis. Zirconium oxide can be recharged by passing a solution containing acetate ions through the zirconium oxide. The activated carbon can be recharged by passing heated water through the activated carbon. The amount of each of the solutions that must be passed through the respective sorbent materials depends on the amount of sorbent material used. As discussed herein, this process may strip the urease from the alumina or silica, necessitating replenishment of the urease.

One skilled in the art will understand that various combinations and/or modifications and variations can be made in the dialysis system depending upon the specific needs for operation. Moreover features illustrated or described as being part of an aspect of the invention may be included in the aspect of the invention, either alone or in combination.

We claim:
1. A dialysis flow loop, comprising:
a sorbent cartridge containing a urease-binding sorbent material positioned on the flow loop;
a urease compartment positioned upstream of the sorbent cartridge on the flow loop and in fluid communication with the sorbent cartridge, wherein the urease compartment is adapted for receiving one or more of a urease pouch, solid urease, and a removable urease cartridge;
wherein the urease compartment comprises a fluid inlet fluidly connectable to a reservoir and a fluid outlet fluidly connectable to the dialysis flow loop upstream of the sorbent cartridge; and
a control system, the control system programmed to meter at least a portion of urease in the urease compartment into the sorbent cartridge.

2. The dialysis flow loop of claim 1, wherein the urease-binding sorbent material is either alumina, silica or a combination thereof, and the urease compartment receives urease.

3. The dialysis flow loop of claim 1, further comprising a urease pump, wherein the urease pump is configured to direct fluid from the urease compartment into the dialysis flow loop.

4. The dialysis flow loop of claim 1, further comprising a dialysis cabinet, wherein the dialysis flow loop is in an interior of the dialysis cabinet and the urease compartment is configured to open to an exterior side of the dialysis cabinet.

5. The dialysis flow loop of claim 4, wherein the urease compartment is slideably disposed on the dialysis cabinet, and the urease compartment is hermetically sealed to the dialysis cabinet when the urease compartment is in a closed position.

6. The dialysis flow loop of claim 1, wherein the sorbent cartridge further comprises one or more sorbent materials selected from the group consisting of activated carbon, hydrous zirconium oxide, zirconium phosphate and ion-exchange resin.

7. The dialysis flow loop of claim 6, wherein at least one of the sorbent materials is rechargeable.

8. The dialysis flow loop of claim 1, further comprising one or more valves positioned between the urease compartment and the sorbent cartridge, wherein the one or more valves are configured to control the amount of fluid moving from the urease compartment to the sorbent cartridge.

9. The dialysis flow loop of claim 1, wherein the urease compartment is adapted for receiving the solid urease.

10. The dialysis flow loop of claim 1, wherein the urease compartment is adapted for receiving the urease pouch.

11. The dialysis flow loop of claim 1, wherein the urease compartment is adapted for receiving the removable urease cartridge.

12. The dialysis flow loop of claim 1, wherein the control system is programmed to meter fluid from the reservoir into the urease compartment prior to metering urease form the urease compartment into the sorbent cartridge.

* * * * *